United States Patent
Iwanowicz

(10) Patent No.: US 11,091,483 B2
(45) Date of Patent: Aug. 17, 2021

(54) PROTEIN KINASE REGULATORS

(71) Applicant: Nanjing Gator Meditech Company, Ltd., Nanjing (CN)

(72) Inventor: Edwin J. Iwanowicz, Rancho Santa Fe, CA (US)

(73) Assignee: Madera Therapeutics, LLC, Cary, NC (US)

( * ) Notice: Subject to any disclaimer, the term of this patent is extended or adjusted under 35 U.S.C. 154(b) by 0 days.

(21) Appl. No.: 16/324,694

(22) PCT Filed: Aug. 14, 2017

(86) PCT No.: PCT/US2017/046715
§ 371 (c)(1),
(2) Date: Feb. 11, 2019

(87) PCT Pub. No.: WO2018/031987
PCT Pub. Date: Feb. 15, 2018

(65) Prior Publication Data
US 2019/0177323 A1  Jun. 13, 2019

Related U.S. Application Data

(60) Provisional application No. 62/374,399, filed on Aug. 12, 2016.

(51) Int. Cl.
*C07D 471/14* (2006.01)
*A61P 35/00* (2006.01)

(52) U.S. Cl.
CPC ............ *C07D 471/14* (2013.01); *A61P 35/00* (2018.01); *C07B 2200/05* (2013.01)

(58) Field of Classification Search
CPC .................................................. C07D 471/14
See application file for complete search history.

(56) References Cited

U.S. PATENT DOCUMENTS

| | | | |
|---|---|---|---|
| 9,376,437 B2 | 6/2016 | Stogniew et al. | |
| 10,526,332 B2 | 1/2020 | Xu et al. | |

FOREIGN PATENT DOCUMENTS

| | | | |
|---|---|---|---|
| WO | 2015153468 | | 10/2015 |
| WO | WO2016123571 | * | 8/2016 |

OTHER PUBLICATIONS

Pinedo et al. (2000).*
McMahon et al. (2000).*

* cited by examiner

*Primary Examiner* — Paul V Ward
(74) *Attorney, Agent, or Firm* — Lewis Kohn & Walker LLP; David M. Kohn

(57) ABSTRACT

Novel compounds and pharmaceutically acceptable salts capable of modulating the activity of kinases, including Akt, ERK and MEK. Such modulation affects biological functions, for example, by inhibiting cell proliferation and/or inducing apoptosis. Also provided are pharmaceutical compositions and medicaments, comprising the compounds or salts of the invention, alone or in combination with other therapeutic agents or palliative agents.

28 Claims, 2 Drawing Sheets

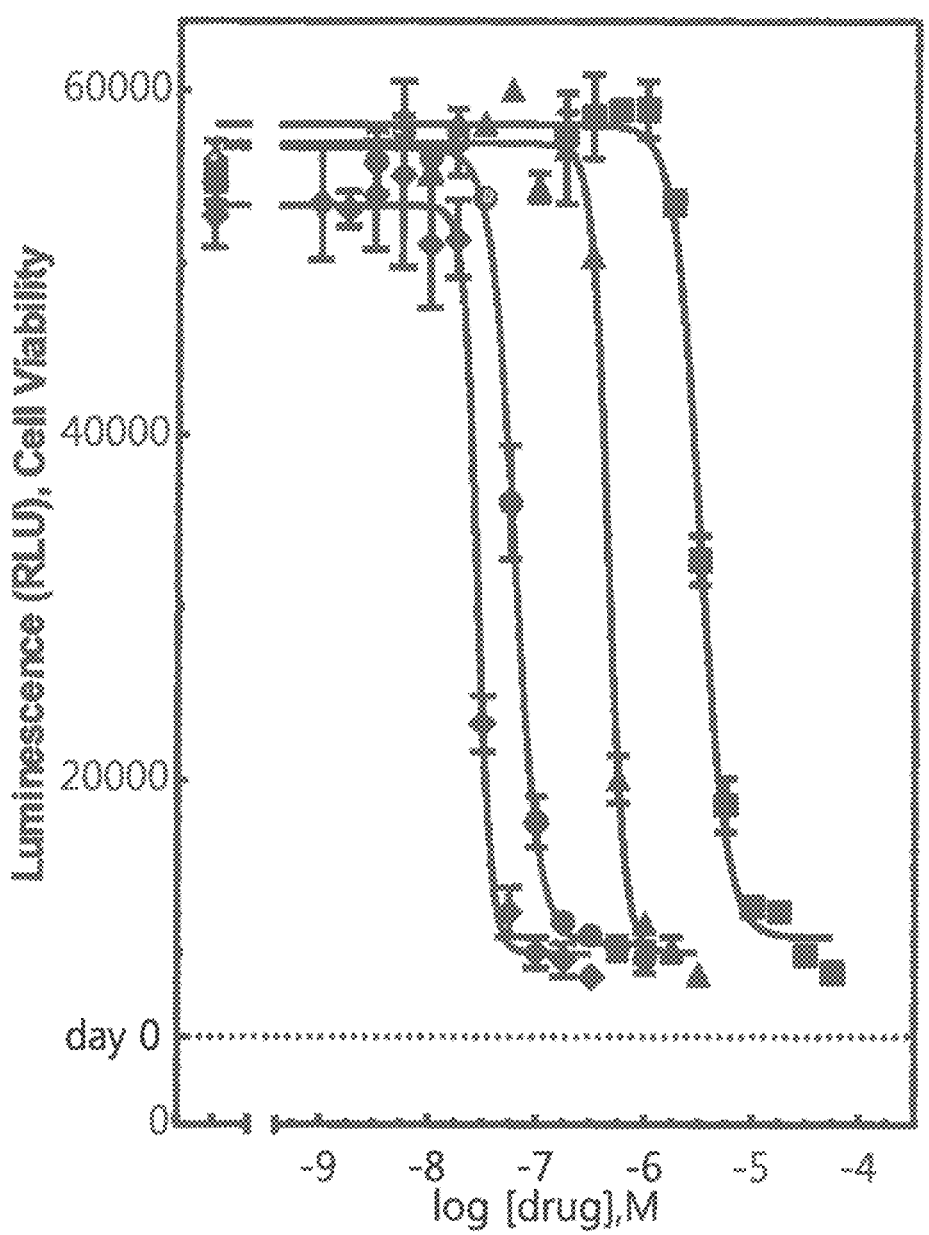
Figure 1: A549 NSCLC Cell Titer Glo Assay
3 day drug treatment

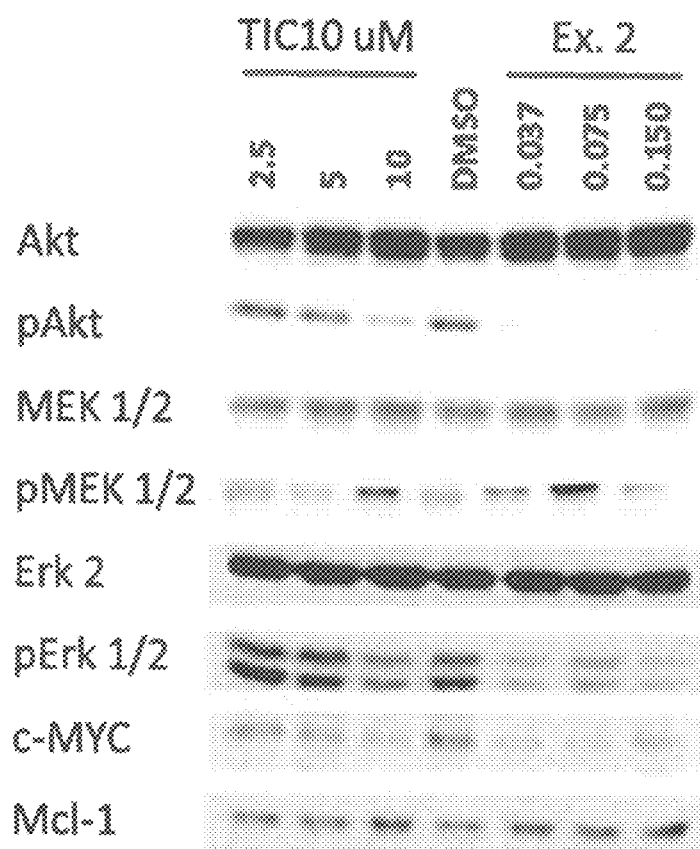
Figure 2 A549 NSCLC Western Blots

PROTEIN KINASE REGULATORS

FIELD OF THE INVENTION

The present invention relates to cyclic compounds and salts thereof, to methods of using such compounds in treating diseases and disorders related to abnormal cell proliferation such as immunological and oncological disorders, and to the pharmaceutical compositions containing such compounds.

BACKGROUND OF THE INVENTION

Kinase signaling pathways, often upregulated in cancer, have been shown to drive many of the hallmark phenotypes of tumor biology. See Hoeflich et al., *J. Clin. Invest.* 2016, 125(5): 1780-1788, and references cited therein. Modulating kinase signaling through direct interaction of a drug with a kinase has led to more than 25 oncology drugs targeting kinases being approved. However, resistance often develops to kinase inhibitors directed toward a single kinase (target kinase) in a biological pathway. Most often the resistance is due to the rise of variants, with advantageous (pro-survival) mutations in the target kinase, and through a more recently appreciated phenomenon of reprogramming of the kinome. See Johnson et al., *Clin. Pham. & Thera.* 2014 95(4) 413-415 and references cited therein. Recently, inactivation of kinases, Akt, ERK and MEK, by a small molecule agent, TIC10 (11-benzyl-7-[(2-methylphenyl)methyl]-2,5,7,11-tetraazatricyclo[7.4.0.0$^{2,6}$]trideca-1 (9),5-dien-8-one), was shown to activate the transcription factor, Foxo3a. See El-Deiry et al., *Sci Transl Med* 2013, 5 171ra117 and references cited therein and El-Deiry et al., *Cancer Res.* 2015 75(7) 1423-1432 and references cited therein. Foxo3a, a member of the Forkhead Box family of transcription factors, regulates the production of Bim (BCL-like protein 11), FasL (Fas ligand/CD95L), TRAIL (TNF-related apoptosis-inducing factor), PUMA (p53 upregulated modulator of apoptosis), p27 (cyclin-dependent kinase inhibitor 1B) and p21 (cyclin-dependent kinase inhibitor 1). These are regulatory factors in cell growth arrest and apoptosis, and regulating these factors has utility in treating abnormal cell proliferation and in particular cancer. Thus, small molecule regulators of Foxo3a activation, via the regulation of Akt and ERK activity, are useful in the treatment of cancer. See Jiang et al., *Biochem. Biophys. Res. Commun.* 2016 476(4) 260-266 and references cited therein and Taylor et al. *Cancer Cell Inter.* 2015 15(1) 1-9, and references cited therein. A patent publication by Oncoceutics, Inc., US 2014/0335048, describes only one compound (Compound 1, FIG. 1) that shows antiproliferative effects on three human cancer cell lines: human colon cancer cell line (HCT116), human breast cancer cell line (MDA-MB-231) and human primary glioblastoma cell line (U87). These data show an approximate 50% cell viability for compound 1, when tested on these cell lines, between 1-10 uM. In a second patent application, WO 2015/153468 A1, by The Scripps Research Institute, shows Oncoceutics' Compound 1 now labeled as Compound 2 and 18 other compounds as having antiproliferative effects on a mouse induced cancer line (RAW264.7). RAW264.7 is a murine macrophage-like cell line that was first described in the literature in the early 1980s and has no specifically engineered characteristic of human cancer. See Rathore et al., *Drug Des. Devel. Ther.* 2014 8, 1911-1922 and references cited therein; see also Adams et al., *BioChem. Biophy. Acta.* 2009 1796(2-2) 140-161 and references cited therein. The most potent of these compounds showed approximately 50% cell viability when tested in vitro at 20 uM (RAW264.7). Murine cancers have a long history in cancer research dating back to the mid 1950s and were widely used by the National Cancer Institute (NCI) and others to identify new cancer drugs. Several studies from the NCI and others demonstrated that this approach had very low clinical predictive value for the treatment of human cancers. See Seymour at al., *Clin. Cancer Res.* 2003, vol 9. 4227-4239 and references cited therein. One study stated that: "Mouse allograft model was not predictive." Thus in 1990, the NCI introduced a disease-oriented Human Tumor Cell Line Screen comprised of 60 cell lines from the most common adult tumors. More recently studies by the NCI and other have shown that studies with human cancer cell lines, both in vitro and in vivo, were generally more predictive than the previous studies with murine cancers. In addition, genetic studies comparing murine and human cancers at times show significant differences. See Depinho et al., *Nat. Rev. Drug Discov.* 2006 5(9), 741-754 and references therein.

"In order to produce its intended effect, a drug must be present at an appropriate concentration in the fluid surrounding the effect site, that is the biophase. More specifically, the drug must be present at the site of action, at sufficient concentration and for an appropriate period of time to have an effect as a therapeutic. Only rarely can drugs be applied directly to the biophase; in most cases drugs need to be transferred from the site of administration to the biophase." See *The Practice of Medicinal Chemistry Third Edition*, Edited by Wermuth Academic Press/Elsevier, Amsterdam, The Netherlands, 2008 and references cited therein.

Many current medicines suffer from poor absorption, distribution, metabolism and/or extretion (ADME) properties that prevent their wider use or limit their use in certain indications. Poor ADME properties are also a major reason for the failure of drug candidates in clinical trials. Often a drug with poor ADME properties lacks sufficient concentration, for an appropriate period of time, at the site of action to have an optimal therapeutic effect. Attempts to compensate for such limitations through higher doses and/or higher frequency of administration of the drug often leads to poor patient compliance and issues such as undesirable metabolites. See U.S. Pat. No. 9,676,760 and references cited therein. Changes in a drug's structure often has unpredictable effects on the drug's ADME profile, including, but not limited to, the effects of deuterium modification on a drug's metabolic properties.

SUMMARY OF THE INVENTION

The present invention provides, in part, novel compounds and pharmaceutically acceptable salts. Such compounds may modulate the activity the kinases: Akt, ERK and MEK thereby affecting biological functions, for example by inhibiting cell proliferation and/or inducing apoptosis. Also provided are pharmaceutical compositions and medicaments, comprising the compounds or salts of the invention, alone or in combination with other therapeutic agents or palliative agents. The present invention also provides, in part, methods for preparing the novel compounds, salts and compositions thereof, and methods of using the foregoing.

A first aspect of the invention is directed to a compound represented by Formula (I):

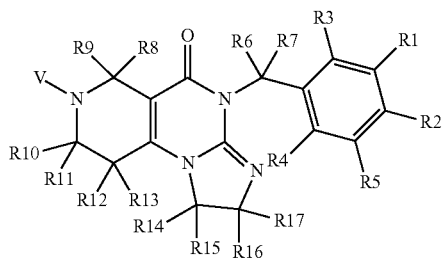
(I)

In Formula I, $R_1$ and $R_2$ are independently selected from the group consisting of hydrogen, —F, —Cl, —Br, —I, —CN, (C1-C3)haloalkoxy, (C1-C4)alkoxy, (C1-C6) alkyl, (C3-C6)cycloalkyl, (C2-C6)alkynyl and (C1-C6)haloalkyl; or alternatively, $R_1$ and $R_2$ may be taken together with the carbon atoms to which they are attached to form a 3-6 membered ring; $R_3$, $R_4$ and $R_5$ are independently selected from the group consisting of hydrogen, halogen, —CN, (C1-C3) haloalkyloxy, (C1-C4)alkoxy, (C1-C6)alkyl, (C3-C6)cycloalkyl, (C2-C6)alkynyl and (C1-C6)haloalkyl; $R_6$ and $R_7$ are each independently selected from the group consisting of hydrogen or methyl; $R_8$ and $R_9$ are each independently selected from the group consisting of hydrogen, halogen and (C1-C3)alkyl; $R_{10}$ and $R_{11}$ are each independently selected from the group consisting of hydrogen, halogen and (C1-C3)alkyl; $R_{12}$ and $R_{13}$ are each independently selected from the group consisting of hydrogen, halogen and (C1-C3) alkyl; $R_{14}$ and $R_{15}$ are each independently selected from the group consisting of hydrogen, halogen, (C3-C6)cycloalkyl and (C1-C3)alkyl; $R_{14}$ and $R_{15}$ together with the carbon atom to which they are attached may form a 3-membered carbocyclic ring; $R_{16}$ and $R_{17}$ are each independently selected from the group consisting of hydrogen, halogen, (C3-C6)cycloalkyl and (C1-C3)alkyl; $R_{16}$ and $R_{17}$ together with the carbon atom to which they are attached may form a 3-membered carbocyclic ring; $R_{15}$ and $R_{16}$ together with the carbons atoms to which they are attached may form a nonaromatic ring having 3 to 6 carbon atoms; V is independently selected from the group consisting of:

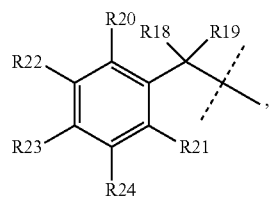
V1

V2

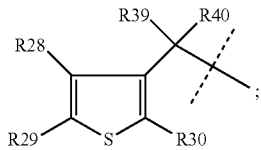
V3

$R_{18}$ and $R_{19}$ are each independently selected from the group consisting of hydrogen or methyl; $R_{20}$ and $R_{21}$ are each independently selected from the group consisting of hydrogen, (C1-C6)alkyl, or halogen; $R_{22}$, $R_{23}$ and $R_{24}$ are required to have at least one occurrence independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —NH$_2$, —SH, —OH, (C1-C6) alkoxy, —NR$_{32}$R$_{33}$, substituted (C1-C6)alkyl, substituted (C3-C9)cycloalkyl, substituted (C3-C9)cycloalkyl(C1-C6) alkyl, substituted (C1-C6)haloalkyl, substituted (C1-C6) alkoxy, (C3-C9)cycloalkyl(C2-C6)alkynyl, (C4-C8)cycloalkenyl, (C4-C8)cycloalkenyl(C1-C6)alkyl, $Z_1$, $Z_2$, $Z_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O) R$_{31}$, and —NR$_{36}$C(O)R$_{31}$; any remaining open position for substitution for $R_{22}$, $R_{23}$ and $R_{24}$ is independently selected from the group consisting of the following: hydrogen, halogen, (C1-C6)alkyl, (C3-C9)cycloalkyl, (C3-C9)cycloalkyl (C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9)cycloalkyl, substituted (C3-C9)cycloalkyl (C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_4$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O) R$_{31}$, and —NR$_{36}$C(O)R$_{31}$; $R_{23}$ and $R_{24}$ may be taken together with the carbon atoms to which they are attached to form a ring; $R_{34}$ and $R_{35}$ may be together with the nitrogen to which they are attached to form a ring; $R_{25}$, $R_{26}$ and $R_{27}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_4$, aryl, heteroaryl, —CN, —NO$_2$, —SR$_{32}$, —C(O)OH, —C(O)OR$_{32}$, —OC(O)OR$_{32}$, (C2-C6) alkynyl, (C2-C8)alkenyl, (C1-C6)haloalkyoxy, —S(O)$_2$ OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$; $R_{28}$, $R_{29}$, and $R_{30}$ are independently selected from the group consisting of the following: hydrogen, halogen, (C1-C6) alkyl, (C3-C9)cycloalkyl, (C3-C9)cycloalkyl(C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9) cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_4$, aryl, heteroaryl, —CN, —NO$_2$, —SR$_{32}$, —C(O)OH, —C(O)OR$_{32}$, —OC(O) OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$; R$_{26}$ and R$_{27}$ together with the carbons atoms to which they are attached may form a ring; R$_{28}$ and R$_{29}$ together with the carbons atoms to which they are attached may form a ring; R$_{31}$ is independently selected from the group consisting of hydrogen, optionally substituted (C1-C8)alkyl, optionally substituted (C3-C9)cycloalkyl, and optionally substituted (C4-C8)alkenyl; R$_{32}$ is independently selected from the group consisting of optionally substituted (C1-C8)alkyl, optionally substituted (C3-C9)cycloalkyl, and optionally substituted (C4-C8)alkenyl; R$_{33}$ is independently selected from the group consisting of optionally substituted (C1-C8)alkyl, optionally substituted (C3-C9)cycloalkyl, and optionally substituted (C4-C8)alkenyl; R$_{34}$ is independently selected from the group consisting of hydrogen, optionally substituted (C1-C8)alkyl, optionally substituted (C3-C9)cycloalkyl, and optionally substituted (C4-C8)alkenyl; R$_{35}$ is independently selected from the group consisting of hydrogen, optionally substituted (C1-C8)alkyl, optionally substituted (C3-C9)cycloalkyl, and optionally substituted (C4-C8)alkenyl; R$_{36}$ is independently selected from the group consisting of hydrogen, optionally substituted (C1-C8)alkyl, optionally substituted (C3-C9)cycloalkyl, and optionally substituted (C4-C8)alkenyl; R$_{37}$ and R$_{38}$ are each independently selected from the group consisting of hydrogen or methyl; R$_{39}$ and R$_{40}$ are each independently selected from the group consisting of hydrogen or methyl; with a proviso that R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen; with a proviso that if R$_2$ is —CH$_3$, —Cl, —Br or —OMe, then R$_1$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen; with a proviso that if R$_3$ is —CH$_3$ or —Cl, then R$_1$, R$_2$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen; with a proviso that if R$_2$ and R$_3$ are —F, then R$_1$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen; with a proviso that if R$_{20}$ is —Br and R$_3$ is —CH$_3$, then R$_1$, R$_2$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{21}$, R$_{22}$, R$_{23}$ and R$_{24}$ cannot simultaneously be hydrogen; Z$_1$ is an optionally substituted 6-membered heterocyclic ring containing 1 or 2 heteroatoms; Z$_2$ is an optionally substituted 4- or 5-membered heterocyclic ring; Z$_3$ is an optionally substituted 7-, 8- or 9-membered heterocyclic ring; Z$_4$ is an optionally substituted heterocyclic ring system with 3 to 11 ring atoms; or a pharmaceutically acceptable salt thereof. In a first preferred embodiment of Formula I, V is V1; and R$_{22}$, R$_{23}$ and R$_{24}$ are required to have at least one occurrence independently selected from the group consisting of the following: —NH$_2$, —SH, —OH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, Z$_1$, Z$_2$, Z$_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$. In a second preferred embodiment of Formula I, V is V1; and R$_{22}$, R$_{23}$ and R$_{24}$ are required to have at least one occurrence independently selected from the group consisting of the following: —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, Z$_2$, Z$_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$. In a third preferred embodiment of Formula I, R$_{15}$ is independently selected from halogen and (C1-C3)alkyl. In a fourth preferred embodiment of Formula I, R$_{16}$ is independently selected from halogen and (C1-C3) alkyl. In a fifth preferred embodiment of Formula I, V is V1; and R$_{22}$ is independently selected from (C2-C6)alkynyl and —CN. In a sixth preferred embodiment of Formula I, R$_2$ is independently selected from halogen and (C1-C2)haloalkyl. In a seventh preferred embodiment of Formula I, V is independently selected from V2 and V3; and R$_{26}$ and R$_{28}$ are independently selected from (C2-C6)alkynyl and —CN. In an eighth preferred embodiment of Formula I, V is independently selected from V2 and V3; and R$_{27}$ and R$_{29}$ are independently selected from (C2-C6)alkynyl and —CN. In a ninth preferred embodiment of Formula I, V is V1; and R$_{22}$, R$_{23}$ and R$_{24}$ are required to have at least one occurrence independently selected from the group consisting of the following: halogen, (C1-C6)alkyl, (C3-C9)cycloalkyl, (C3-C9)cycloalkyl(C1-C6)alkyl, (C1-C6)haloalkyl, —NH$_2$, —SH, —OH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, Z$_1$, Z$_2$, Z$_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$. In a first set of preferred alternatives within the ninth preferred embodiment of Formula I, R$_1$ is independently selected from hydrogen and —F; R$_2$ is independently selected from halogen, (C1-C6)haloalkyl; R$_3$ is independently selected from hydrogen and —F; R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$ and R$_{20}$ are simultaneously hydrogen; R$_{20}$ and R$_{21}$ are independently selected from hydrogen and —F. In a second set of preferred alternatives within the ninth preferred embodiment of Formula I, R$_1$ is independently selected from hydrogen and —F; R$_2$ is independently selected from —CF$_3$, —CHF$_2$, —F, —Cl and —Br; R$_{22}$ is independently selected from —CN, and —(C2)alkynyl; R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{23}$, and R$_{24}$ are simultaneously hydrogen. In a third set of preferred alternatives within the ninth preferred embodiment of Formula I, R$_2$ is independently selected from —CF$_3$, —Cl and —Br; R$_{22}$ is independently selected from halogen; R$_1$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{23}$, and R$_{24}$ are simultaneously hydrogen. Preferred species of Formula I include the following compounds:

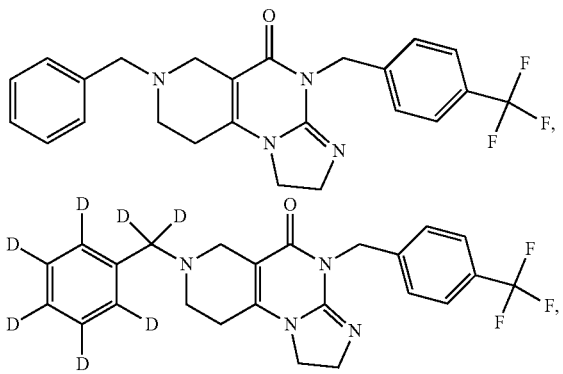

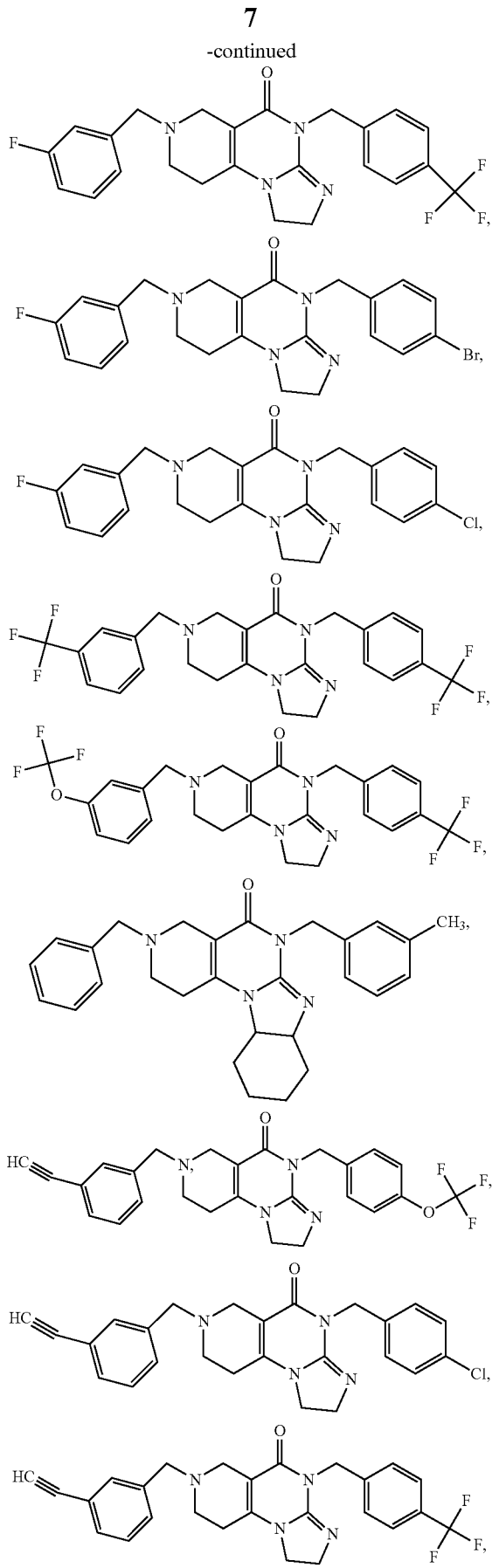

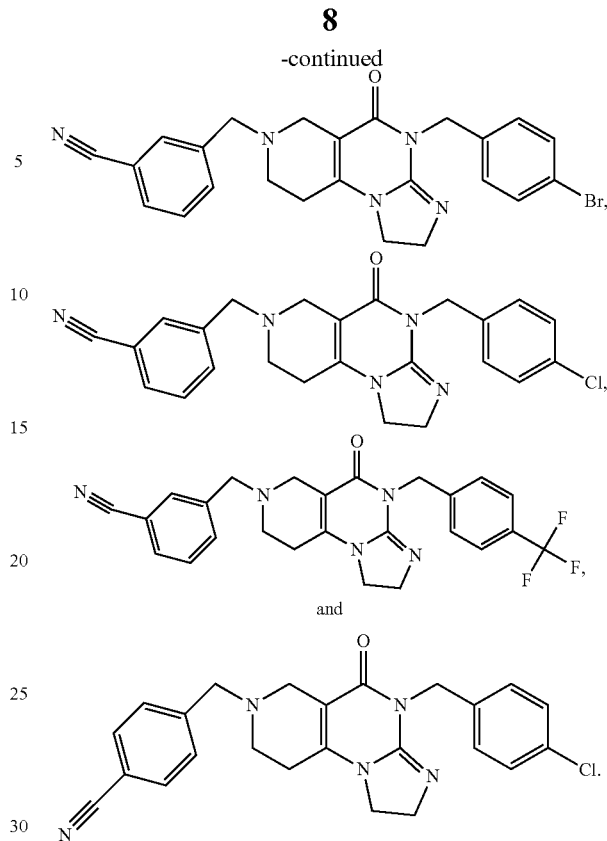

In second aspect, the invention provides a method for the treatment of abnormal cell growth, including cancer, in a subject comprising administering to the subject a therapeutically effective amount of a compound of the invention, or a pharmaceutically acceptable salt. More particularly, the method comprises the step of administering an effective amount of a compound represented by formula (I), or a pharmaceutically acceptable salt thereof. In a first preferred mode of the second aspect of the invention, the method for the treatment of cancer in a subject comprises the step of administering an effective amount of a compound of the first preferred embodiment of Formula I, or a pharmaceutically acceptable salt thereof. In a second preferred mode of the second aspect of the invention, the method for the treatment of cancer in a subject comprises the step of administering an effective amount of a compound of the second preferred embodiment of Formula I, or a pharmaceutically acceptable salt thereof. In a third preferred mode of the second aspect of the invention, the method for the treatment of cancer in a subject comprises the step of administering an effective amount of a compound of the third preferred embodiment of Formula I, or a pharmaceutically acceptable salt thereof. In a fourth preferred mode of the second aspect of the invention, the method for the treatment of cancer in a subject comprises the step of administering an effective amount of a compound of the fourth preferred embodiment of Formula I, or a pharmaceutically acceptable salt thereof. In a fifth preferred mode of the second aspect of the invention, the method for the treatment of cancer in a subject comprises the step of administering an effective amount of a compound of the fifth preferred embodiment of Formula I, or a pharmaceutically acceptable salt thereof. In a sixth preferred mode of the second aspect of the invention, the method for the treatment of cancer in a subject comprises the step of administering an effective amount of a compound of the sixth preferred embodiment of Formula I, or a pharmaceutically acceptable salt thereof. In a seventh preferred mode of the second aspect of the invention, the method for the treatment of cancer in a subject comprises the step of administering an effective amount of a compound of the seventh preferred embodiment of Formula I, or a pharmaceutically acceptable salt thereof. In an eighth preferred mode of the second aspect of the invention, the method for the treatment of cancer in a subject comprises the step of administering an effective amount of a compound of the eighth preferred embodiment of Formula I, or a pharmaceutically acceptable salt thereof. In a ninth preferred mode of the second aspect of the invention, the method for the treatment of cancer in a subject comprises the step of administering an effective amount of a compound of the ninth preferred embodiment of Formula I, or a pharmaceutically acceptable salt thereof. In a tenth preferred mode of the second aspect of the invention, the method for the treatment of cancer in a subject comprises the step of administering an effective amount of a compound of the first set of alternative embodiments of the ninth preferred embodiment of Formula I, or a pharmaceutically acceptable salt thereof. In an eleventh preferred mode of the second aspect of the invention, the method for the treatment of cancer in a subject comprises the step of administering an effective amount of a compound of the second set of alternative embodiments of the ninth preferred embodiment of Formula I, or a pharmaceutically acceptable salt thereof. In a twelfth preferred mode of the second aspect of the invention, the method for the treatment of cancer in a subject comprises the step of administering an effective amount of a compound of the third set of alternative embodiments of the ninth preferred embodiment of Formula I, or a pharmaceutically acceptable salt thereof. In a thirteenth preferred mode of the second aspect of the invention, the method for the treatment of cancer in a subject comprises the step of administering an effective amount of any of the preferred species of Formula I, or a pharmaceutically acceptable salt thereof.

A third aspect of the invention is directed to a pharmaceutical composition comprising a compound represented by Formula I, or a pharmaceutically acceptable salt thereof, in combination with a pharmaceutically acceptable carrier or excipient. In a first preferred embodiment of this third aspect of the invention, the pharmaceutical composition comprises a compound of the first preferred embodiment of Formula I, or a pharmaceutically acceptable salt thereof, in combination with a pharmaceutically acceptable carrier or excipient. In a second preferred embodiment of this third aspect of the invention, the pharmaceutical composition comprises a compound of the second preferred embodiment of Formula I, or a pharmaceutically acceptable salt thereof, in combination with a pharmaceutically acceptable carrier or excipient. In a third preferred embodiment of this third aspect of the invention, the pharmaceutical composition comprises a compound of the third preferred embodiment of Formula I, or a pharmaceutically acceptable salt thereof, in combination with a pharmaceutically acceptable carrier or excipient. In a fourth preferred embodiment of this third aspect of the invention, the pharmaceutical composition comprises a compound of the fourth preferred embodiment of Formula I, or a pharmaceutically acceptable salt thereof, in combination with a pharmaceutically acceptable carrier or excipient. In a fifth preferred embodiment of this third aspect of the invention, the pharmaceutical composition comprises a compound of the fifth preferred embodiment of Formula I, or a pharmaceutically acceptable salt thereof, in combination with a pharmaceutically acceptable carrier or excipient. In a sixth preferred embodiment of this third aspect of the invention, the pharmaceutical composition comprises a compound of the sixth preferred embodiment of Formula I, or a pharmaceutically acceptable salt thereof, in combination with a pharmaceutically acceptable carrier or excipient. In a seventh preferred embodiment of this third aspect of the invention, the pharmaceutical composition comprises a compound of the seventh preferred embodiment of Formula I, or a pharmaceutically acceptable salt thereof, in combination with a pharmaceutically acceptable carrier or excipient. In a eighth preferred embodiment of this third aspect of the invention, the pharmaceutical composition comprises a compound of the eighth preferred embodiment of Formula I, or a pharmaceutically acceptable salt thereof, in combination with a pharmaceutically acceptable carrier or excipient. In a ninth preferred embodiment of this third aspect of the invention, the pharmaceutical composition comprises a compound of the ninth preferred embodiment of Formula I, or a pharmaceutically acceptable salt thereof, in combination with a pharmaceutically acceptable carrier or excipient. In a tenth preferred embodiment of this third aspect of the invention, the pharmaceutical composition comprises a compound of the first set of alternative embodiments of the ninth preferred embodiment of Formula I, or a pharmaceutically acceptable salt thereof, in combination with a pharmaceutically acceptable carrier or excipient. In a eleventh preferred embodiment of this third aspect of the invention, the pharmaceutical composition comprises a compound of the second set of alternative embodiments of the ninth preferred embodiment of Formula I, or a pharmaceutically acceptable salt thereof, in combination with a pharmaceutically acceptable carrier or excipient. In a twelfth preferred embodiment of this third aspect of the invention, the pharmaceutical composition comprises a compound of the third set of alternative embodiments of the ninth preferred embodiment of Formula I, or a pharmaceutically acceptable salt thereof, in combination with a pharmaceutically acceptable carrier or excipient. In a thirteenth preferred embodiment of this third aspect of the invention, the pharmaceutical composition comprises any of the preferred species of Formula I, or a pharmaceutically acceptable salt thereof, in combination with a pharmaceutically acceptable carrier or excipient.

In frequent embodiments of the methods provided herein, the abnormal cell growth is cancer. In some embodiments, the methods provided result in one or more of the following: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In frequent embodiments, the abnormal cell growth is cancer and the subject is a human.

In some embodiments, the methods described herein further comprise administering to the subject an amount of an anti-cancer therapeutic agent or a palliative agent, which amounts may be together effective in treating said abnormal growth. In some embodiments, the one or more anti-cancer therapeutic agent is selected from anti-tumor agents, anti-angiogenesis agents, signal transduction inhibitors, and antiproliferative agents, which amounts are together effective in treating said abnormal cell growth. In some such embodiments, the anti-tumor agent is selected from the group consisting of mitotic inhibitors, alkylating agents, antimetabolites, intercalating antibodies, growth factor inhibitors, radiation, cell cycle inhibitors, enzymes, topoisomerase inhibitors, biological response modifiers, antibodies, cytotoxics, anti-hormones, and anti-androgens.

Each of the embodiments below describing the invention envisions within the scope the pharmaceutically acceptable salts of the compounds of the invention. Accordingly, the phrase "or a pharmaceutically acceptable salt thereof" is implicit in the description of all compounds described herein.

BRIEF DESCRIPTION OF DRAWINGS

FIG. 1 illustrates a graph depicting the results of a 3 day drug treatment with experimental and control compounds on A549 NSCLC cells by cell titer glo assay.

FIG. 2 illustrates Western blots from A549 NSCLC cells treated with experimental and control compounds.

DETAILED DESCRIPTION OF THE INVENTION

The present invention may be understood more readily by reference to the following detailed description of the preferred embodiments of the invention and the Examples included herein.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the structure. If a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" portions of "hydroxyalkyl," "fluoroalkyl," "—O-alkyl," etc, unless otherwise indicated.

As used herein, and throughout this disclosure, the following terms, unless otherwise indicated, shall be understood to have the following meanings:

A "patient" or "subject" is a human or non-human mammal. In one embodiment, a patient or subject is a human. In another embodiment, a patient or subject is a chimpanzee.

The term "therapeutically effective amount" as used herein, refers to an amount of the compound of Formula (I) and/or additional therapeutic agent, or a composition thereof that is effective in producing the desired therapeutic, ameliorative, inhibitory or preventative effect when administered to a patient suffering from cancer or another disease or disorder of undesirable cell proliferation. In the combination therapies of the present invention, a therapeutically effective amount can refer to each individual agent or to the combination as a whole, wherein the amounts of all agents administered are together effective, but wherein the component agent of the combination may not be present individually in an effective amount. In reference to the treatment of cancer, a therapeutically effective amount, refers to that amount which has the effect of (1) reducing the size of the tumor, (2) inhibiting (that is slowing to some extent, preferably stopping) tumor metastasis, (3) inhibiting to some extent (preferably stopping) tumor growth or tumor invasiveness and/or (4) relieving to some extent (or preferably, eliminating) one or more signs or symptoms associated with cancer.

The term "preventing" as used herein with respect to cancer or a disease or disorder of undesirable cell proliferation, refers to reducing the likelihood or rate of disease or disorder progression.

The use of a dashed or dotted line signifies a single bond between said molecular fragment and another defined molecular fragment. For example, the selection of V1 for V in Formula (I) yields the following structure:

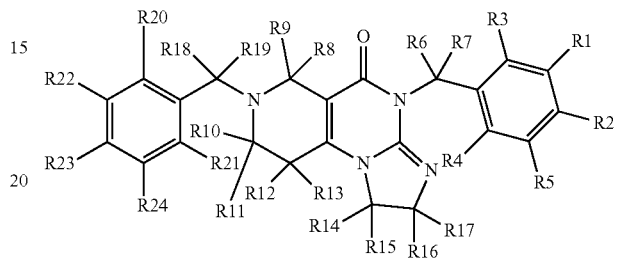

The term "alkyl" as used herein, refers to an aliphatic hydrocarbon group having one of its hydrogen atoms replaced with a bond having the specified number of carbon atoms. The alkyl group may be straight chain or branched chain groups. Alkyl substituents typically contain 1 to 20 carbon atoms "(C1-C20)alkyl", preferably 1-12 carbon atoms "(C1-C12)alkyl", more preferably 1 to 8 carbon atoms "(C1-C8)alkyl", or 1 to 6 carbon atoms "(C1-C6)alkyl", or 1 to 4 carbon atoms "(C1-C4)alkyl". In different embodiments, an alkyl group contains from 7-12 carbon atoms "(C7-C12)alkyl" or from 7 to 20 carbon atoms "(C7-C20)alkyl". Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. Alkyl groups described herein as optionally substituted ("optionally substituted alkyl") may be substituted by one or more substituent groups, which are selected independently unless otherwise indicated. Alkyl groups described herein as substituted alkyl ("substituted alkyl") will be substituted with one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, preferably from 1 to 4 optional substituents and more preferably from 1 to 3 optional substituents. For example, an optionally substituted ethylene group is "optionally substituted (C2)alkyl" and a substituted ethylene group is "substituted (C2)alkyl".

Suitable substituent groups for both, "optionally substituted alkyl" and "substituted alkyl" include, but are not limited to (C3-C8)cycloalkyl, 3-12 membered heterocyclyl, (C6-C12)aryl, 5-12 membered heteroaryl, halo, =O (oxo), =S (thiono), =N—CN, =N—OR$^X$, =NR$^X$, —CN, —C(O)R$^X$, —CO$_2$R$^X$, —C(O)NR$^X$R$^Y$, —SR$^X$, —SOR$^X$, —SO$_2$R$^X$, —SO$_2$NR$^X$R$^Y$, —NO$_2$, —NR$^X$R$^Y$, —NR$^X$C(O) R$^Y$, —NR$^X$C(O)NR$^X$R$^Y$, —NR$^X$C(O)OR$^X$, —NR$^X$SO$_2$R$^Y$, —NR$^X$SO$_2$NR$^X$R$^Y$, —OR$^X$, —OC(O)R$^X$ and —OC(O) NR$^X$R$^Y$; where in each R$^X$ and R$^Y$ is independently hydrogen, (C1-C6)alkyl, (C2-C6)alkenyl, (C2-C6)alkynyl, (C3-C6)cycloalkyl, 3-12 membered heterocyclyl, (C6-C12)aryl, or 5-12 membered heteroaryl, or R$^X$ and R$^Y$ may be taken together with the nitrogen atom to which they are attached to form a 3-12 membered heterocyclyl or 5-12 membered heteroaryl system, each optionally containing 0, 1 or 2 additional heteroatoms; each $R^X$ and $R^Y$ is optionally substituted with 1 to 3 substituents independently selected from the group consisting of halo, =O, —CN, —C(O)R', —CO$_2$R', —C(O)NR'$_2$, —SO$_2$R', —NR'$_2$, —OR', wherein each R' is independently hydrogen, (C1-C6)alkyl, (C3-C6) cycloalkyl, or 3-12 membered heterocyclyl. However, suitable substituent for "substituted alkyl" does not include hydrogen.

"Alkenyl" refers to an alkyl group, as defined herein, consisting of at least two carbon atoms and at least one carbon-carbon bond. Typically, alkenyl groups have 2 to 20 carbon atoms "(C2-C20)alkenyl", preferably 2 to 12 carbon atoms "(C2-C12)alkenyl", more preferably 2 to 8 carbon atoms "(C2-C8)alkenyl", or 2 to 6 carbon atoms "(C2-C6) alkenyl", or 2 to 4 carbon atoms "(C2-C4)alkenyl". Representative examples include, but are not limited to, ethenyl, 1-propenyl, 2-propenyl, 1-, 2-, or 3-butenyl, and the like. Suitable substituent groups for alkenyl are as described herein for, "optionally substituted alkyl" and "substituted alkyl".

"Alkynyl" refers to an alkyl group, as defined herein, consisting of at least two carbon atoms and at least one carbon-carbon triple bond. Alkynyl groups have 2 to 20 carbon atoms "(C2-C20)alkynyl", preferably 2 to 12 carbon atoms "(C2-C12)alkynyl", more preferably 2 to 8 carbon atoms "(C2-C8)alkynyl", or 2 to 6 carbon atoms "(C2-C6) alkynyl", or 2 to 4 carbon atoms "(C2-C4)alkynyl". Representative examples include, but are not limited to, ethynyl, 1-propynyl, 2-propynyl, 1-, 2-, or 3-butynyl, and the like. Alkynyl groups may be unsubstituted or substituted. Suitable substituent groups for alkynyl are as described herein for, "optionally substituted alkyl" and "substituted alkyl".

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —CH$_2$F, —CHF$_2$, and —CF$_3$. The term "(C1-C3) fluoroalkyl" refers to a fluoroalkyl group having from 1 to 3 carbon atoms. The term "(C1)fluoroalkyl" refers to —CH$_2$F, —CHF$_2$, and —CF$_3$.

The term "aryl" as used herein, refers to an aromatic monocyclic or multicyclic ring system comprising from 6 to about 14 carbon atoms. In one embodiment, an aryl group contains from about 6 to 10 carbon atoms ($C_6$-$C_{10}$ aryl). In another embodiment, an aryl group is phenyl. Non-limiting examples of aryl groups include phenyl and naphthyl.

The term "cycloalkyl," as used herein, refers to a saturated ring containing the specified number of ring carbon atoms, and no heteroatoms. Cycloalkyl substituents typically contain 3 to 8 carbon atoms "(C3-C8)cycloalkyl", preferably 3-7 carbon atoms "(C3-C7)cycloalkyl", more preferably 3 to 6 carbon atoms "(C3-C6)cycloalkyl", or 3 to carbon atoms "(C3-C5)cycloalkyl". Non-limiting examples of monocyclic cycloalkyls include cyclopropyl, cyclobutyl, cyclopentyl, and cyclohexyl. Cycloalkyl groups described herein as optionally substituted ("optionally substituted cycloalkyl") may be substituted by one or more substituents groups, which are selected independently unless otherwise indicated. Cycloalkyl groups described herein as substituted cycloalkyl ("substituted cycloalkyl") will be substituted with one or more substituent groups, which are selected independently unless otherwise indicated. The total number of substituent groups may equal the total number hydrogen atoms on the cycloalkyl moiety, to the extent such substitution makes chemical sense. Optionally substituted cycloalkyl groups typically contain from 1 to 6 optional substituents, preferably from 1 to 4 optional substituents and more preferably from 1 to 3 optional substituents. For example, an optionally substituted cyclopropyl group is "optionally substituted (C3)cycloalkyl" and a substituted cyclopropyl group is "substituted (C2)cycloalkyl". In one embodiment a cycloalkyl group contains 3 to 9 carbon atoms, "(C3-C9) cycloalkyl". In another embodiment a substituted cycloalkyl group contains 3 to 9 carbon atoms, "substituted (C3-C9) cycloalkyl". Suitable substituent groups for cycloalkyl are as described herein for, "optionally substituted alkyl" and "substituted alkyl".

The term "cycloalkenyl" as used herein, refers to partially unsaturated carbocyclic ring system containing the specified number of carbon atoms. Cycloalkenyl substituents typically contain 4 to 8 carbon atoms "(C4-C8)cycloalkenyl" and preferably 5-6 carbon atoms "(C5-C6)cycloalkenyl". Non-limiting examples of monocyclic cycloalkenyls include cyclobutenyl, cyclopentenyl, cyclohexenyl, and cycloheptenyl. Cycloalkenyl groups described herein may be optionally substituted ("cycloalkenyl") with one or more substituent groups, which are selected independently unless otherwise indicated. The total number of substituent groups may equal the total number of hydrogen atoms on the cycloalkenyl moiety, to the extent such substitution makes chemical sense. Optionally substituted cycloalkenyl groups typically contain from 1 to 6 optional substituents, preferably from 1 to 4 optional substituents and more preferably from 1 to 3 optional substituents. For example, a cyclopentenyl group is "(C5)cycloalkenyl" and an optionally substituted cyclopentenyl group is "optionally substituted (C5) cycloalkenyl". In one embodiment a cycloalkenyl group contains 4 to 8 carbon atoms, "(C4-C8)cycloalkenyl". Suitable substituent groups for cycloalkenyl are as described herein for, "optionally substituted alkyl" and "substituted alkyl".

The term "cycloalkylalkyl" as used herein, refers to a cycloalkyl ring, typically a (C3-C9)cycloalkyl, which is connected to the base molecule through an alkylene linker of 1 to 6 carbon atoms "(C1-C6)alkylene". Cycloalkylalkyl groups are described by the number of carbon atoms in the carbocyclic ring and the number of carbon atoms in the linker. Cycloalkylalkyl groups described herein as optionally substituted ("optionally substituted cycloalkylalkyl") may be substituted by one or more substituent groups, which are selected independently unless otherwise indicated. Cycloalkylalkyl groups described herein as substituted cycloalkylalkyl ("substituted cycloalkylalkyl") will be substituted with one or more substituent groups, which are selected independently unless otherwise indicated. The total number of substituent groups may equal the total number of hydrogen atoms on the cycloalkylalkyl moiety, to the extent such substitution makes chemical sense. Optionally substituted cycloalkylalkyl groups typically contain from 1 to 6 optional substituents, preferably from 1 to 4 optional substituents and more preferably from 1 to 3 optional substituents. In one embodiment a cycloalkyl group contains 3 to 9 carbon atoms and the linker alkyl group contains 1 to 6 carbon atoms, "(C3-C9)cycloalkyl(C1-C6)alkyl". For example, cyclopropylethyl group is "(C3)cycloalkyl(C2) alkyl" and an optionally substituted cyclopropylethyl group is "optionally substituted (C3)cycloalkyl(C2)alkyl". In addition, a substituted cyclopropylethyl group is "substituted (C3)cycloalkyl(C2)alkyl". Suitable substituent groups for cycloalkylalkyl are as described herein for, "optionally substituted alkyl" and "substituted alkyl".

The term "cycloalkenylalkyl" as used herein, refers to a cycloalkenyl ring, typically a (C4-C8)cycloalkenyl, which is connected to the base molecule through an alkylene linker of 1 to 6 carbon atoms "(C1-C6)alkylene". Cycloalkenylalkyl groups are described by the number of carbon atoms in the carbocyclic ring and the number of carbon atoms in the linker. Thus a "(C5)cycloalkyenyl(C1)alkyl" group is a cyclopentenyl group connected to the base molecule though a methylene group (—CH$_2$—). Cycloalkenylalkyl groups described herein may be optionally substituted by one or more substituent groups, which are selected independently unless otherwise indicated. The total number of substituent groups may equal the total number of hydrogen atoms on the cycloalkenylalkyl moiety, to the extent such substitution makes chemical sense. Optionally substituted cycloalkenylalkyl groups typically contain from 1 to 6 optional substituents, preferably from 1 to 4 optional substituents and more preferably from 1 to 3 optional substituents. In one embodiment a cycloalkenyl group contains 4 to 8 carbon atoms and the linker alkyl group contains 1 to 6 carbon atoms, "(C4-C8)cycloalkenyl(C1-C6)alkyl". For example, cyclopentenylethyl group is "(C5)cycloalkenyl(C2)alkyl" and an optionally substituted cyclopentenylethyl group is "optionally substituted (C5)cycloalkenyl(C2)alkyl". Suitable substituent groups for cycloalkenylalkyl are as described herein for, "optionally substituted alkyl" and "substituted alkyl".

In some instances, substituted alkyl groups may be specifically named with reference to the substituent group. For example "haloalkyl" refers to an alkyl group having the specified number of carbon atoms that is substituted by one or more halo substituents, and typically contain 1 to 6 carbon atoms and 1, 2 or 3 halo atoms (i.e., "(C1-C6)haloalkyl"). Thus, a (C1-C4)haloalkyl group includes trifluoromethyl (—CF$_3$) and difluoromethyl (—CF$_2$H). Haloalkyl groups described herein as optionally substituted ("optionally substituted haloalkyl") may be substituted by one or more substituent groups, which are selected independently unless otherwise indicated. Haloalkyl groups described herein as substituted haloalkyl ("substituted haloalkyl") will be substituted with one or more substituent groups, which are selected independently unless otherwise indicated. The total number of substituent groups may equal the total number of hydrogen atoms on the haloalkyl moiety, to the extent such substitution makes chemical sense. Optionally substituted haloalkyl groups typically contain from 1 to 6 optional substituents, preferably from 1 to 4 optional substituents and more preferably from 1 to 3 optional substituents. For example, an optionally substituted halopropyl group is "optionally substituted (C3)haloalkyl" and a substituted halopropyl group is "substituted (C3)haloalkyl". In one embodiment a cycloalkyl group contains 1 to 6 carbon atoms, "(C1-C6)haloalkyl". In another embodiment a substituted haloalkyl group contains 1 to 6 carbon atoms, "substituted (C1-C6)haloalkyl". Suitable substituent groups for haloalkyl are as described herein for, "optionally substituted alkyl" and "substituted alkyl".

"Alkoxy" refers to a monovalent —O-alkyl group, wherein the alkyl portion has the specified number of carbon atoms. The alkyl portion of the alkoxy group, may be straight chain or branched chain groups. Alkoxy groups typically contain 1 to 8 carbon atoms "(C1-C8)alkoxy", or 1 to 6 carbon atoms "(C1-C6)alkoxy" or 1 to 4 carbon atoms "(C1-C4)alkoxy". Non-limiting examples of alkoxy groups include methoxy, ethoxy, n-propoxy, isopropoxy, n-butoxy and t-butoxy. Alkoxy groups described herein as optionally substituted ("optionally substituted alkoxy") may be substituted by one or more substituent groups, which are selected independently unless otherwise indicated. Alkoxy groups described herein as substituted alkoxy ("substituted alkoxy") will be substituted with one or more substituent groups, which are selected independently unless otherwise indicated. The total number of substituent groups may equal the total number of hydrogen atoms on the alkoxy moiety, to the extent such substitution makes chemical sense. Optionally substituted alkoxy groups typically contain from 1 to 6 optional substituents, preferably from 1 to 4 optional substituents and more preferably from 1 to 3 optional substituents. For example, an optionally substituted ethoxy group is "optionally substituted (C2)alkoxy" and a substituted butoxy group is "substituted (C4)alkoxy". In one embodiment an alkoxy group contains 1 to 6 carbon atoms, "(C1-C6)alkoxy". In another embodiment a substituted alkoxy group contains 1 to 6 carbon atoms, "substituted (C1-C6) alkoxy". Suitable substituent groups for alkoxy are as described herein for, "optionally substituted alkyl" and "substituted alkyl".

The term "haloalkoxy" refers to a monovalent —O-haloalkyl group wherein the alkyl portion has the specified number of carbon atoms that are substituted by one or more halo substituents, and typically contain 1 to 6 carbon atoms and 1, 2 or 3 halo atoms (i.e., "(C1-C6)haloalkoxy") In some instances, substituted alkyl groups may be specifically named with reference to the substituent group. For example "haloalkoxy" refers to an alkyl group having the specified number of carbon atoms. Thus, a (C1-C4)haloalkoxy group includes trifluoromethoxy (—OCF$_3$). Haloalkoxy groups described herein may be substituted by one or more substituent groups, which are selected independently unless otherwise indicated. The total number of substituent groups may equal the total number of hydrogen atoms on the haloalkyl moiety, to the extent such substitution makes chemical sense. Optionally substituted haloalkoxy groups typically contain from 1 to 3 optional substituents and preferably from 1 to 2 optional substituents. In one embodiment a haloalkoxy group contains 1 to 6 carbon atoms, "(C1-C6)haloalkoxy". An example of a substituted haloalkoxy group contains 1 to 6 carbon atoms, "(C1-C6) haloalkoxy". Suitable substituent groups for haloalkyloxy are as described herein for, "optionally substituted alkyl" and "substituted alkyl".

The term "halo" as used herein, means —F, —Cl, —Br or —I. In one embodiment, a halo group is —Cl. In another embodiment, a halo group is —Br.

The term "acyl" as used herein means —C(O)alkyl or —C(O)cycloalkyl. The alkyl group may be straight chain or branched chain groups. Alkyl substituent of an acyl group typically contain 1 to 20 carbon atoms, preferably 1-12 carbon atoms, more preferably 1 to 8 carbon atoms, 1 to 6 carbon atoms, or 1 to 4 carbon atoms. The cycloalkyl substituent of an acyl group typically contain 3 to 8 carbon atoms, preferably 3-7 carbon atoms, more preferably 3 to 6 carbon atoms, or 3 to 5 carbon atoms. The alkyl and cycloalkyl moieties may be substituted. Suitable substituent groups are as described herein for, "optionally substituted alkyl" and "substituted alkyl".

The term "aryl" or "aromatic" refers to an optionally substituted monocyclic biaryl or fused bicyclic ring systems, having the well-known characteristics of aromaticity, wherein at least one ring contains a completely conjugated pi-electron system. Typically, aryl groups contain 6 to 20 carbon atoms, "(C6-20)aryl" as ring members, preferably 6 to 14 carbon atoms "(C6-C14)aryl" or more preferably 6 to 12 carbon atoms "(C6-C12)aryl". Fused aryl groups may include an aryl ring (e.g., a phenyl ring) fused to another aryl ring, or fused to a saturated or partially unsaturated carbocyclic or heterocyclic ring. The point of attachment to the base molecule on such fused aryl ring systems may be a carbon atom of the aromatic portion or a carbon or nitrogen atom of the non-aromatic portion of the ring system. Example, without limitation, of aryl groups include phenyl, biphenyl, naphthyl, anthracenyl, phenanthrenyl, indanyl, indenyl, and tetrahydronaphthyl. The aryl group may be unsubstituted or substituted as further described herein.

The term "heteroaryl" or heteroaromatic" as used herein, refers to an aromatic monocyclic or multicyclic ring system comprising about 5 to about 14 ring atoms, wherein from 1 to 4 of the ring atoms is independently N, O, or S and the remaining ring atoms are carbon atoms. These systems having the well-known characteristics of aromaticity. Heteroaryl rings are attached to the base molecule via a ring atom of the heteroaromatic ring, such that aromaticity is maintained. The inclusion of a heteroatom permits aromaticity in 5-membered rings as well as 6 membered rings. In one embodiment, a heteroaryl group has 5 to 10 ring atoms. In another embodiment, a heteroaryl group is a monocyclic ring system and has 5 to 6 ring atoms. In another embodiment, a heteraryl group is a bicyclic ring system. The term "heteroaryl" also includes a heteroaryl, as defined above, fused to a heterocyclyl as defined below. The term "heteroaryl" also encompasses a heteroaryl group, as defined above, which is fused to a benzene, a cyclohexadiene or a cyclohexane ring. Non-limiting examples of heteroaryls include pyridyl, pyrazinyl, furanyl, thienyl, pyrimidinyl, pyridine (including N-substituted pyridines), isoxazolyl, isothiazolyl, oxazolyl, oxadiazolyl, thiazolyl, pyrazonyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and alike. In one embodiment, a heteroaryl group is optionally substituted, as described herein, "optionally substituted heteroaryl".

The terms "heterocyclyl", "heterocyclic" or "heteroalicyclic" may be used interchangeably herein, to refer to a non-aromatic saturated or partially saturated monocyclic or multicyclic ring system containing 3 to 11 ring atoms, wherein from 1 to 4 of the ring atoms are independently O, S, or N and the remainder of the ring atoms are carbon atoms. In one embodiment, a heterocyclic group is monocyclic and has 6 ring atoms, "6-membered heterocyclic ring". In another embodiment, a heterocyclic group is a monocyclic and has 6 ring atoms with either 1 or 2 ring atoms being a heteroatom, "6-membered heterocyclic ring containing 1 or 2 heteroatoms". In another embodiment, a heterocyclic group is monocyclic and has either 4 or 5 ring atoms, "4- or 5-membered heterocyclic ring". In another embodiment, a heterocyclic group has 7, 8 or 9 ring atoms, "7-, 8- or 9-membered heterocyclic ring". In another embodiment, a heterocyclic group is bicyclic. A heterocyclic group can be joined to the rest of the molecule via a ring carbon or ring nitrogen atom. The nitrogen or sulphur atom of the heterocyclyl can be optionally oxidized to the corresponding N-oxide, S-oxide or S,S-dioxide. Non-limiting examples of the monocyclic heterocyclic rings include oxetanyl, piperidyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone and the like. Heterocyclic groups may be unsubstituted or substituted, when specified, by the same groups suitable for alkyl, aryl or heteroaryl. In one embodiment a heterocyclic ring contains 6 atoms and is substituted with 1 to 4 groups as defined herein, "6-membered heterocyclic ring substituted with one to four groups". In addition, ring nitrogen atoms may be optionally substituted, when specified, by groups suitable for an amine, e.g., alkyl, acyl, carbamoyl, sulfonyl substituents, etc., and ring S atoms may be optionally substituted by 1 or 2 oxo groups (i.e., $S(O)_q$, where q is 0, 1 or 2). In one embodiment a 4 or 5 membered heterocyclic ring is optionally substituted, as given above, "optionally substituted 4- or 5-membered heterocyclic ring". In another embodiment, a 7, 8- or 9-membered heterocyclic ring is optionally substituted, as given above, "optionally substituted 7-, 8- or 9-membered heterocyclic ring".

Aryl, heteroaryl and heterocyclic moieties described herein as optionally substituted ("optionally substituted") may be substituted by one or more substituent groups, which are selected independently unless otherwise indicated. Aryl, heteroaryl and heterocyclic moieties described herein as substituted ("substituted") are substituted by one or more substituent groups, which are selected independently unless otherwise indicated. Optionally substituted aryl, heteroaryl or heterocyclic groups typically contain from 1 to 5 optional substituents, sometimes 1 to 4 optional substituents, preferably 1 to 3 optional substituents, or more preferably 1-2 optional substituents. Substituted aryl, heteroaryl or heterocyclic groups contain at least one substituent as described herein and may optionally contain up to 5 total substituents each independently selected.

Substituent groups suitable for aryl, heteroaryl and heterocyclic rings include, but are not limited to: (C1-C8)alkyl, (C2-C8)alkenyl, (C2-C8)alkynyl, (C3-C8)cycloalkyl, 3-12 membered heterocyclyl, (C6-C12)aryl, 5-12 membered heteroaryl, halo, =O (oxo), =S (thiono), =N—CN, =N—$OR^X$, =$NR^X$, —CN, —C(O)$R^X$, —$CO_2R^X$, —C(O)$NR^XR^Y$, —$SR^X$, —$SOR^X$, —$SO_2R^X$, —$SO_2NR^XR^Y$, —$NO_2$, —$NR^XR^Y$, —$NR^XC(O)R^Y$, —$NR^XC(O)NR^XR^Y$, —$NR^XC(O)OR^X$, —$NR^XSO_2R^Y$, —$NR^XSO_2NR^XR^Y$, —$OR^X$, —OC(O)$R^X$ and —OC(O)$NR^XR^Y$; where in each $R^X$ and $R^Y$ is independently hydrogen, (C1-C6)alkyl, (C2-C6)alkenyl, (C2-C6)alkynyl, (C3-C6)cycloalkyl, 3-12 membered heterocyclyl, (C6-C12)aryl, or 5-12 membered heteroaryl, or $R^X$ and $R^Y$ may be taken together with the nitrogen atom to which they are attached to form a 3-12 membered heterocyclyl or 5-12 membered heteroaryl system, each optionally containing 0, 1 or 2 additional heteroatoms; each $R^X$ and $R^Y$ is optionally substituted with 1 to 3 substituents independently selected from the group consisting of halo, =O, —CN, —C(O)R', —$CO_2R'$, —C(O)$NR'_2$, —$SO_2R'$, —$NR'_2$, —OR', wherein each R' is independently hydrogen, (C1-C6)alkyl, (C3-C6)cycloalkyl, or 3-12 membered heterocyclyl. However, suitable substituent for "substituted alkyl" does not include hydrogen.

"Unsubstituted amino" refers to a group —$NH_2$. Where the amino is described as substituted or optionally substituted, the term includes groups of the form —$NR^XR^Y$, where each $R^X$ and $R^Y$ is independently selected from hydrogen, (C1-C8)alkyl, (C3-C9)cycloalkyl, alkynyl, heterocyclyl, acyl, aryl, heteroaryl, thioacyl, cycloalkylalkyl, arylalkyl, or heteroalkylalkyl, in each case having the specified number of atoms and optionally substituted as described herein. Typically, alkyl substituents on amines contain 1 to 8 carbon atoms, preferably 1 to 6 carbon atoms, or more preferably 1 to 4 carbon atoms. The term also includes forms wherein $R^X$ and $R^Y$ are taken together with the nitrogen to which they are attached to form a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms. The term, as described above, extends to the amino residue of another functional group (for example, —C(O)NR$_X$R$_Y$, —S(O)$_2$NR$_X$R$_Y$, and alike). In one embodiment, R$_X$ and R$_Y$ of —NR$_X$R$_Y$; of —C(O)NR$_X$R$_Y$, may be taken together with the nitrogen to which they are attached to form a ring (a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms). In another embodiment, R$_X$ and R$_Y$ of —NR$_X$R$_Y$; of —S(O)$_2$NR$_X$R$_Y$, may be taken together with the nitrogen to which they are attached to form a ring (a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms).

Two adjacent substituents on a ring may be taken together, with the atoms to which they are attached, to form a ring. The term "together with the carbons atoms to which they are attached may form a ring" is defined herein to mean two adjacent residues residing on a ring may be combined together with the carbon atoms to which they are attached to form a 3-12 membered heterocyclyl, a 3-7 membered carbocyclyl, or a 5-12 membered heteroaryl ring, each of which may be optionally substituted as described herein for heterocyclyl or heteroaryl rings. Thus formed heterocyclyl and heteroaryl rings may contain 1 to 3 additional heteroatoms selected from N, O, and S as ring members, (provided that such rings do not contain contiguous oxygen atoms or contiguous sulphur atoms). Non-limiting examples derived from a suitably substituted phenyl moieties of compound of Formula (I) include, but are not limited to, benzofuranyl, benzothiophenyl, indolyl, benzimidazolyl, indazolyl, benzotrizolyl, indazolyl, quinolinyl, isoquinolinyl, cinnolinyl, azaquinazoline, quinoxalinyl, 2,3-dihydro-1H-indenyl, phthalanyl, 2,3-dihydrobenzofuryl, benzodioxoyl, benzodioxanyl, and the like. Non-limiting examples derived from two substituents on a hetereocyclyl ring include, but are not limited to:

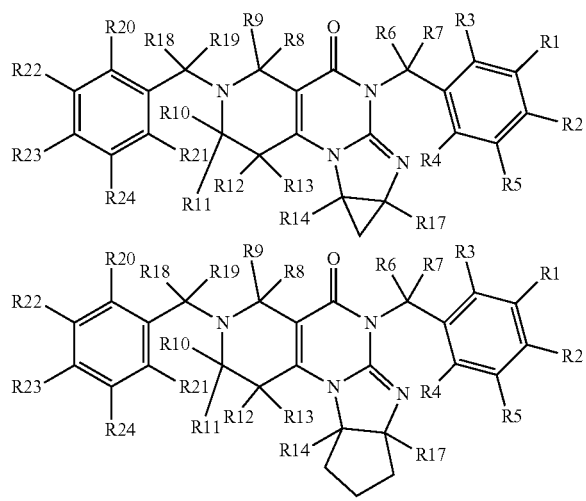

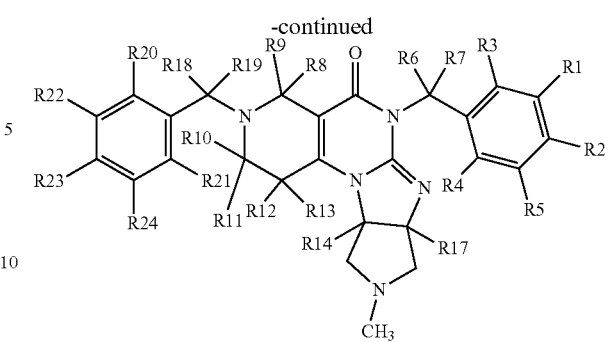

and alike. Non-limiting examples derived from two substituents on an aryl ring include, but are not limited to:

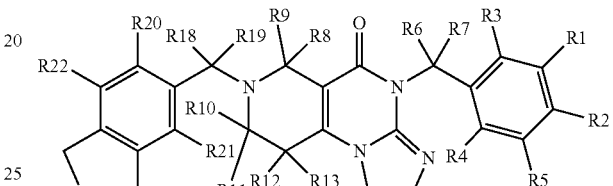

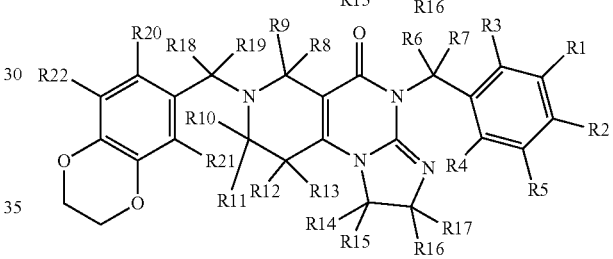

and alike.

The term "substituted" means that one or more hydrogen atoms of the designated are replaced with a selection from the indicated group, provided that the atoms' normal valencies under the existing circumstances are not exceeded, and that the substitution results in a stable compound. By "stable compound" or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form" as used herein, refers to the physical state of a compound after the compound is isolated from a synthetic process (eg., from a reaction mixture), a natural source, or a combination thereof. The term "in purified form" also refers to the physical state of a compound after the compound is obtained from a purification process or processes described herein or well-known to the skilled artisan (e.g., chromatography, recrystallization and the like).

It should be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms.

The compounds of Formula (I) may contain one or more stereogenic centers and can thus occur as racemates, racemic mixtures, single enantiomers, diastereomeric mixtures and individual disatereomers. Each such asymmetric center will independently produce two optical isomers and it is intended that all of the possible optical isomers and diastereomers in mixtures and as pure or partially purified compounds are included within the ambit of this invention.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). Enriching in a particular isotope may provide an advantageous characteristic(s), for example enriching for deuterium may afford certain therapeutic advantages, such as increasing in vivo half-life or reducing dosages. In addition, isotopic enrichment may also enrich a compound's usefulness in the characterization of biological samples. Compounds enriched in a specific isotope may be prepared via synthetic methods described herein and methods known to those skilled in the art by using reagents and starting material enriched with the specific isotope.

Prodrugs of the compounds of the invention are contemplated herein. The term "prodrug", as employed herein, denotes a compound which upon administration to a subject, undergoes chemical conversion by metabolic or chemical processes to yield a compound of Formula (I). Prodrugs may have beneficial properties, such as but not limited to, the enhancement of absorption and/or oral bioavailability.

The compounds of Formula (I) may in some cases form salts which are also with the scope of this invention. Reference to a compound of the formula (I) herein is understood to include reference to salts thereof, unless otherwise noted. The term "salt(s)" as used herein denotes acidic and/or basic salts formed with inorganic and/or organic acids and bases. Zwitterionic (internal or inner salts) are included within the term "salt(s)" as used herein (and may be formed, for example, where the R substituents comprise an acid moiety such as a carboxyl group). Also included herein are quaternary salts ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the Formula (I) may be formed, for example, by reacting a compound of Formula (I) by reacting a compound of Formula (I) with an equivalent amount of an acid or base in a medium such as one the allows for the precipitation of the salt (example, ether) or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example by P. Stahl et al, Camille G. (eds.) Handbook of Pharmaceutical Salts. Properties, Selection and Use. (2002) Zurich: Wiley-VCH. This disclosure is incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes compounds of Formula (I) in all their isolated forms.

Compounds of the Invention

In one aspect, the invention provides a compound of Formula (I):

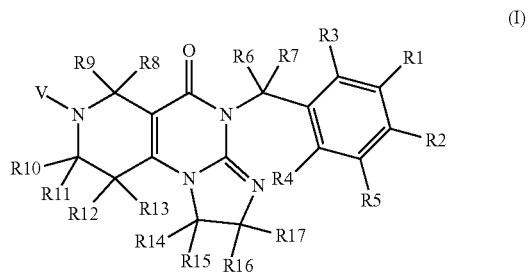

In Formula I, $R_1$ and $R_2$ are independently selected from the group consisting of hydrogen, —F, —Cl, —Br, —I, —CN, (C1-C3)haloalkoxy, (C1-C4)alkoxy, (C1-C6) alkyl, (C3-C6) cycloalkyl, (C2-C6)alkynyl or (C1-C6)haloalkyl; or alternatively, $R_1$ and $R_2$ may be taken together with the carbon atoms to which they are attached to form a 3-6 membered ring; $R_3$, $R_4$ and $R_5$ are independently selected from the group consisting of hydrogen, halogen, —CN, (C1-C3) haloalkyloxy, (C1-C4)alkoxy, (C1-C6)alkyl, (C3-C6)cycloalkyl, (C2-C6)alkynyl and (C1-C6)haloalkyl; $R_6$ and $R_7$ are each independently selected from the group consisting of hydrogen or methyl; $R_8$ and $R_9$ are each independently selected from the group consisting of hydrogen, halogen and (C1-C3)alkyl; $R_8$ and $R_9$ together with the carbon atom to which they are attached may form a 3-membered carbocyclic ring; $R_{10}$ and $R_{11}$ are each independently selected from the group consisting of hydrogen, halogen and (C1-C3) alkyl; $R_{10}$ and $R_{11}$ together with the carbon atom to which they are attached may form a 3-membered carbocyclic ring; $R_{12}$ and $R_{13}$ are each independently selected from the group consisting of hydrogen, halogen and (C1-C3)alkyl; $R_{12}$ and $R_{13}$ together with the carbon atom to which they are attached may form a 3-membered carbocyclic ring; $R_{14}$ and $R_{15}$ are each independently selected from the group consisting of hydrogen, halogen, (C3-C6)cycloalkyl and (C1-C3)alkyl; $R_{14}$ and $R_{15}$ together with the carbon atom to which they are attached may form a 3-membered carbocyclic ring; $R_{16}$ and $R_{17}$ are each independently selected from the group consisting of hydrogen, halogen, (C3-C6)cycloalkyl and (C1-C3)alkyl; $R_{16}$ and $R_{17}$ together with the carbon atom to which they are attached may form a 3-membered carbocyclic ring; $R_{15}$ and $R_{16}$ together with the carbons atoms to which they are attached may form a ring; V is independently selected from the group consisting of:

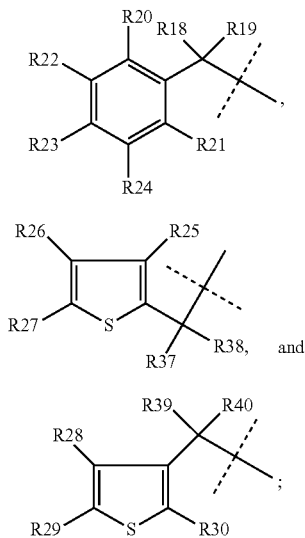

$R_{18}$ and $R_{19}$ are each independently selected from the group consisting of hydrogen or methyl; $R_{20}$ and $R_{21}$ are each independently selected from the group consisting of hydrogen, (C1-C6)alkyl, or halogen; $R_{22}$, $R_{23}$ and $R_{24}$ are required to have at least one occurrence independently selected from the following: hydrogen, halogen, (C1-C6)alkyl, (C3-C9)cycloalkyl, (C3-C9)cycloalkyl(C1-C6)alkyl, (C1-C6)haloalkyl, —NH$_2$, —SH, —OH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_1$, $Z_2$, $Z_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$; Any remaining open position for substitution for $R_{22}$, $R_{23}$ and $R_{24}$ is independently selected from the following: hydrogen, halogen, (C1-C6)alkyl, (C3-C9)cycloalkyl, (C3-C9)cycloalkyl(C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_4$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$; $R_{23}$ and $R_{24}$ may be taken together with the carbon atoms to which they are attached to form a ring; $R_{34}$ and $R_{35}$ may be together with the nitrogen to which they are attached to form a ring; $R_{25}$, $R_{26}$ and $R_{27}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_4$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$; $R_{26}$ and $R_{27}$ together with the carbons atoms to which they are attached may form a ring; $R_{28}$ and $R_{29}$ together with the carbons atoms to which they are attached may form a ring; $R_{31}$ is independently selected from the group consisting of hydrogen, optionally substituted (C1-C8)alkyl, optionally substituted (C3-C9)cycloalkyl, and optionally substituted (C4-C8)alkenyl; $R_{32}$ is independently selected from the group consisting of optionally substituted (C1-C8)alkyl, optionally substituted (C3-C9)cycloalkyl, and optionally substituted (C4-C8)alkenyl; $R_{33}$ is independently selected from the group consisting of optionally substituted (C1-C8)alkyl, optionally substituted (C3-C9)cycloalkyl, and optionally substituted (C4-C8)alkenyl; $R_{34}$ is independently selected from the group consisting of hydrogen, optionally substituted (C1-C8)alkyl, optionally substituted (C3-C9)cycloalkyl, and optionally substituted (C4-C8)alkenyl; $R_{35}$ is independently selected from the group consisting of hydrogen, optionally substituted (C1-C8)alkyl, optionally substituted (C3-C9)cycloalkyl, and optionally substituted (C4-C8)alkenyl; $R_{36}$ is independently selected from the group consisting of hydrogen, optionally substituted (C1-C8)alkyl, optionally substituted (C3-C9)cycloalkyl, and optionally substituted (C4-C8)alkenyl; $R_{37}$ and $R_{38}$ are each independently selected from the group consisting of hydrogen or methyl; $R_{39}$ and $R_{40}$ are each independently selected from hydrogen or methyl; wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ cannot simultaneously be hydrogen; wherein $R_2$ is —CH$_3$, —Cl, —Br or —OMe then $R_1$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ cannot simultaneously be hydrogen; wherein $R_3$ is —CH$_3$ or —Cl, then $R_1$, $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ cannot simultaneously be hydrogen; wherein $R_2$ and $R_3$ are —F then $R_1$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ cannot simultaneously be hydrogen. $Z_1$ is an optionally substituted 6-membered heterocyclic ring containing 1 or 2 heteroatoms; $Z_2$ is an optionally substituted 4- or 5-membered heterocyclic ring; $Z_3$ is an optionally substituted 7-, 8- or 9-membered heterocyclic ring; $Z_4$ is an optionally substituted heterocyclic ring system with 3 to 11 ring atoms; or a pharmaceutically acceptable salt thereof.

In frequent embodiments, of Formula (I), $R_3$, $R_4$, $R_6$, $R_7$, $R_8$, $R_9$ $R_{10}$, $R_{11}$, $R_{12}$, $R_{13}$, $R_{14}$, $R_{15}$, $R_{16}$, $R_{17}$ $R_{18}$, $R_{19}$ are hydrogen.

In some embodiments, of Formula (I), $R_2$ is —Cl, —Br or —CF$_3$.

In some embodiments of Formula (I), $R_2$ is —Cl and $R_3$, $R_4$, $R_6$, $R_7$, $R_8$, $R_9$ $R_{10}$, $R_{11}$, $R_{12}$, $R_{13}$, $R_{14}$, $R_{15}$, $R_{16}$, $R_{17}$ $R_{18}$, $R_{19}$ are hydrogen.

In some embodiments of Formula (I), $R_2$ is —Br and $R_3$, $R_4$, $R_6$, $R_7$, $R_8$, $R_9$ $R_{10}$, $R_{11}$, $R_{12}$, $R_{13}$, $R_{14}$, $R_{15}$, $R_{16}$, $R_{17}$ $R_{18}$, $R_{19}$ are hydrogen.

In some embodiments of Formula (I), $R_2$ is —CF$_3$ and $R_3$, $R_4$, $R_6$, $R_7$, $R_8$, $R_9$ $R_{10}$, $R_{11}$, $R_{12}$, $R_{13}$, $R_{14}$, $R_{15}$, $R_{16}$, $R_{17}$ $R_{18}$, $R_{19}$ are hydrogen.

In some embodiments of Formula (I), $R_{22}$ is (C2-C6) alkynyl.

In some embodiments of Formula (I), $R_{22}$ is (C2)alkynyl and $R_2$ is —CF$_3$.

In some embodiments of Formula (I), $R_{22}$ is (C2)alkynyl and $R_2$ is —Cl.

In some embodiments of Formula (I), $R_{22}$ is (C2)alkynyl and $R_2$ is —Br.

Dosage Forms and Regimens

Administration of compounds of the invention may be affected by any method that enables delivery of the compounds to the site of action. These methods include oral routes, intraduodenal routes, parenteral injection (including intravenous, subcutaneous, intramuscular, or infusion), topical and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dose. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention may be dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention. It is to be noted that dosage values may vary with the type and severity of the condition to be alleviated, and may include single or multiple doses. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the claimed composition. For example, doses may be adjusted based on pharmacokinetic or pharmacodynamics parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the active compound.

The pharmaceutically acceptable carrier may comprise any conventional pharmaceutical carrier or excipient. The choice of carrier and/or excipient, will to a large extent, depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of material, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution, suspension or emulsion, for topical administration as an ointment or crease, or for rectal administration as a suppository.

Exemplary parenteral administration forms include solutions or suspensions of an active compound in a sterile aqueous solution, for example, aqueous propylene glycol or dextrose solutions. Such dosage forms may be suitably buffered, if desired.

The pharmaceutical composition may be in unit dosage forms suitable for single administration of precise amounts.

Pharmaceutical compositions suitable for the delivery of active agents and methods for their preparation will be readily apparent to those skilled in the art. Such compositions and methods for their preparation may be found, for example, in "Remington's Pharmaceutical Sciences", 19$^{th}$ Edition (Mack Publishing Company, 1995), the disclosure of which is incorporated herein by reference in its entirety.

Compounds of the invention may be administered orally. Oral administration may involve swallowing, so that the compound enters the gastrointestinal tract, buccal or sublingual administration may be employed by which the compounds enters the blood stream directly from the mouth.

Formulations suitable for oral administration include solid formulations such as tablets, capsules containing particulates, liquids, or powders. Lozenges (including liquid filled), chews, multi- and nano-particulates, gels solid solution, liposome, films, ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the active agent may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl, cellulose and hydroxypropyl methylcellulose. Tablets may also contain diluents, such as lactose, mannitol, xylitol, dextrose, sucrose, sorbitol, microcrystalline cellulose, starch, and dibasic calcium phosphate dehydrate.

Tablets may also optionally include surface active agents such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Exemplary tablets may contain up to about 80 wt % active agents for about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in detail in "pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Suitable modified release formulations are described in U.S. Pat. No. 6,106,864. Details of other suitable release technologies such as high energy dispersions and osmotic and coated particles may be found in Verma et al, Pharmaceutical Technology On-line 25(2), 1-14 (2001). This disclosure of this reference is incorporated herein by reference in its entirety.

It is understood that compounds of Formula (I) can be formulated as a di-salt.

Parenteral Administration

Compounds of the invention may also be administered directly into the blood stream, into muscle, or into an internal organ. Suitable means for parenteral administration including intravenous, intraarterial, intraperitoneal, intrathecal, intraventricular, intraurethral, intracranial, intramuscular and subcutaneous. Suitable devices for parenteral administration include needle injectors, needle-free injectors and infusion techniques.

Parenteral formulations are typically aqueous solutions which may contain excipients such as salts, carbohydrates and buffering agents (preferably to a pH of 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may potentially be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may potentially be formulated as a solid, semi-solid, or thixotropic liquid for administration as an implanted depot providing modified release of the active compound. Examples of such formulations include drug-coated stents and PGLA microspheres.

The compounds of the invention may also potentially be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers bandages and microemulsions.

Dosage

The amount of the active compound administered will be dependent on the subject being treated, the severity of the disorder or condition, the rate of administration, the disposition of the compound and the discretion of the prescribing physician. However, the effective dose is typically in the range of about 0.001 to about 100 mg per kg body weight per day, preferably 0.01 to about 35 mg/kg/day, in a single or divided doses. For a human, this would amount to about 0.07 to about 700 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Combination Therapy

As used herein, the term "combination therapy" refers to the administration of a compound of the invention together with at least one additional pharmaceutical or medicinal agent (e.g., an anti-cancer agent), either sequentially or simultaneously.

As noted above, the compounds of the invention may potentially be used in combination with one or more additional anti-cancer agents, which are described below. When a combination therapy is used, the one or more additional anti-cancer agent may be administered sequentially or simultaneously with the compound of the invention. In one embodiment, the additional anti-cancer agent is administered to a mammal (subject, patient) prior to administration of the compound of the invention. In another embodiment, the additional anti-cancer agent is administered to the mammal after administration of the compound of the invention. In another embodiment, the additional anti-cancer agent is administered to the mammal simultaneously with the administration of the compound of the invention.

The invention also relates to a pharmaceutical composition for the treatment of abnormal cell growth in a mammal, including a human, which comprises an amount of a compound of the invention, as defined herein, in combination with one or more (preferably one to three) anti-cancer agents selected from a group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In one embodiment of the present invention the anti-cancer agent used in conjunction with a compound of the invention and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCbeta inhibitors, COX-2 inhibitors, integrins, MMP-2 (matrix-metalloproteinase 2) inhibitors, and MMP-9 (matrix-metalloproteinase 9) inhibitors.

Preferred anti-angiogenesis agents include sunitinib (Sutent™), bevacizumab (Avastin™), axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™) (AE 941), tetra-thiomolyb-data (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which may be used in conjuction with a compound of the invention and pharmaceutical compositions described herein include celecoxib (Celebrex™), parecoxib (Dynastat™), deracoxib (SC 59046), lumiracoxib (Preige™), valdecoxic (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltarn™), indomethacin (Indocin™), sulindac (Clinoril™), tolmetin (Tolectin™), etodolac (Lodine™), ketorolac (Toradol™), and oxaprozin (DayPro™).

Other anti-angiogenesis agents include ABT 510 (Abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™, rebimastat (BMS 275291), catumaxomab, (Removab™), lenalidomide (Revlimid™), squalamine (EVIZON™), thalidomide (Thalomid™), Ukrain™ (NSC 631570), Vitaxin™ (MEDI 522), and zoledronic acid (Zomata™).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EgF inhibitors, ErbB-1 (EGFR) inhibitors, ErbB-2 inhibitors, pan-erb inhibitors, IGF1R inhibitors, MEK (1,2) inhibitors, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitors, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzmab (Herceptin™), sunitinib (Sutent™), imatinib (Gleevec™), Trametinib™ (GSK1120212) and Cobimetinib™ (XL518).

Additional examples of signal transduction inhibitors which may be used in conjunction with a compound of the invention and pharmaceutical compositions described herein include BMS 214662, lonafarnib (Sarasar™), pelitrexol (AG 2037), matuzumab (EMD 7200), nimotuzumab (TheraCIM h-$R_3$™), panitumumab (Vectibix™), Vandetanib (Zactima™), pazopanib (SB 786034), BIBW 2992 (Boehringer Ingelheim), and Cervene™ (TP 38).

Other examples of signal transduction inhibitors include Canertinib (CI 1033), pertuzumab (Omnitarg™), Lapatinib (Tycerb™), pelitinib (EKB 569), miltefosine (Miltefosin™), BMS 599626, Lapuleucel-T (Neuvenge™), NeuVax™), Osidem™ (IDM 1), mubritinib (TAK-165), Panitumumab (Vectibix™), lapatinib (Tycerb™), pelitinib (EKB 569), and pertuzumab (Omnitarg™).

Other examples of signal transduction inhibitors include ARRY 142886, everolimus (Certican™), zotarolimus (Endeavor™), temsirolimus (Torisel™), and VX 680 (Vertex).

This invention contemplates the use of a compound of the invention together with antineoplastic agents. Antineoplastic agents include, but are not limited to, hormonal, anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose), polymerase-1 (PARP-1) inhibitors microtubulin inhibitors, antibiotics, spindle inhibitors, platinum-coordinated compounds, gene therapeutic agents, antisense oligonucleotides, vascular targeting agents (VTAs) and statins.

Examples of antineoplastic agents used in combination therapy with a compound of the invention, include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486) selective estrogen receptor modulators (SERMs, such as tamoxifen, raloxifene, lasofoxifene, afimoxifene, arzoxifene, bazedoxifene, fispemifene, ormeloxifene, ospemifene, tesmilifene, toremifene, trilostance and CHF 4227 (Cheisi), selective estrogen-receptor downregulators (SERDs, such as fulvestrant), exemestane (Aromasin™), anastrozole (Arimidex™), atamestane, fadrozole, letrozole (Femara), gonadotropin-releasing hormone (GnRH, also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, abarelix, goserelin, leuprorelin, triptorelin, bicalutamide, tamoxifen, exemestane, anastrozole, fadrozole, fromestane, letrozole, and combinations thereof.

Other example of antineoplastic agents used in combination with a compound of the invention include, but are not limited to, suberolanilide hydroxamic acid (SAHA™, Merck), depsipeptide (FR901228), G2M-777, MS-275, pivaloyloxymethyl butyrate and PXD-101/Onconase™ (ranpimase), PS-341, Valcade™ (bortezomib), 9-aminocamptothecin, belotecan, BN-80915, camptothecin, diflomotecan, edotecarin, exatecan, gimatecan, 10-hydroxycamptothecin, irinotecan HCl (Camptosar™), lurtotecan, Orathecin™ (rubitecan, Supergen™), SN-38, topotecan, camptothecin, 10-hydroxycamptothecin, 9-aminocamptothecin, irinotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard™ (dexrazoxane), nitrogen mustard N-oxide, cyclophosphamide, AMD-473, altretamine, Ap-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating agents such as cisplatin. Paraplatin (carboplatin), eptaplatin, lobaplatin, nedaplatin, Eloxatin™ (oxaliplatin), streptozocin, satrplatin, and combinations thereof.

The invention also contemplates the use of a compound of the invention together with dihydrofolate reductase inhibitors (for example methotrexate and NeuTrexin™ (trimetresate glucoronate)), purine antagonist (for example 6-mercaptopurine riboside, mercaptopurine, 6-thioguanine, cladribine, clofarabine (Clolar™), fludarabine, nelarabine, and raltitrexed), pyrimidine antagonists (for example, 5-fluorouracil (5-FU), Alimta™ (premetrexed disodium), capecitabine (Xeloda™), cytosine, Arabinoside, Gemzar™ (gemcitabine), Tegafur™ (UFT Orzel™ or UForal™ and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynyl-cytidine) and other antimetabolites such as eflomithine, hydroxyurea, leucovorin, nolatrexed, triapine, trimetrexate, ABT-472, Ino-1001, KU-0687 and GPI 18180 and combinations thereof.

Additional examples of antineoplastic agents used in combination therapy with a compound of the invention, optionally with one or more other agents include, but are not limited to, Advexin™, Genasense (oblimersen, Genta), Combretastatin A4P (CA4P), Oxi4503, AVE-8062, ZD-6126, TZT 1027, atorvastatin (Lipitor™), pravastatin (Pravachol™), lovastatin (Mevacor™), simvastatin (Zocor™), fluvastatin (Lescol™), cerivastatin (Baycol™), rosuvastatin (Crestor™), niacin (Advicor™), caduet and combinations thereof.

Another embodiment of the present invention of particular interest relates to a method for the treatment of breast cancer in a human in need of such treatment, comprising administering to said human an amount of a compound of the invention, in combination with one or more (preferably one to three) anti-cancer agents selected from the group consisting of trastuzumab, tamoxifen, docetaxel, paclitaxel, capecitabine, gemcitabine, vinorelbine, exmestane, letrozole and anastrozole.

Therapeutic Methods and Uses

The invention further provides therapeutic methods and uses comprising administering a compound of the invention, or pharmaceutically acceptable salt thereof, alone or in combination with one or more other therapeutic agents or palliative agents.

In one aspect, the invention provides a method for the treatment of abnormal cell growth in a subject comprising administering to the subject a therapeutically effective amount of a compound of the invention, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, in combination with an amount of an anti-tumor agent, which amounts are together effective in treating said abnormal growth. In some embodiments, the anti-tumor agent is selected from the group consisting of mitotic inhibitors, alkylating agents, antimetabolites, intercalating antibiotics, growth factor inhibitors, radiation, cell cycle inhibitors, enzymes, topoisomerase inhibitors, biological response modifiers, antibodies, cytotoxics, anti-hormones and anti-androgens.

In another aspect, the invention provides a method of inhibiting cancer cell proliferation in a subject, comprising administering to the subject a compound of the invention, or pharmaceutically acceptable salt thereof, in an amount effective to inhibit cell proliferation.

In another aspect, the invention provides a method of inhibiting cancer cell invasiveness in a subject, comprising administering to the subject a compound of the invention, or pharmaceutically acceptable salt thereof, in an amount effective to inhibit cell proliferation.

In another aspect, the invention provides a method of inducing apoptosis in cancer cells in a subject, comprising administering to the subject a compound of the invention, or pharmaceutically acceptable salt thereof, in an amount effective to inhibit cell proliferation.

In another aspect, the invention provides a method of inducing apoptosis in a subject, comprising administering to the subject a compound of the invention, or pharmaceutic acceptable salt thereof, in an amount effective to inhibit cell proliferation.

In frequent embodiments of the methods provided herein, the abnormal cell growth is cancer, wherein said cancer is selected from the group consisting of basal cell cancer, medulloblastoma cancer, liver cancer, rhabdomyosarcoma, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In some embodiments, the cells are in a tissue or tumor, and the tissue or tumor may be in a subject, including a human.

Cancers treated using methods and compositions described herein are characterized by abnormal cell proliferation including, but not limited to, metastasis, pre-neoplastic hyperproliferation, cancer in situ, and neoplasms. Compounds of this invention can be for prophylaxis in addition to amelioration of signs and/or symptoms of cancer. Examples of cancers treated by the compounds of the present invention include, but are not limited to, breast cancer, CNS cancers, colon cancer, prostate cancer, leukemia, lung cancer and lymphoma.

Methods of Preparing the Compounds of Formula (I)

The compounds of this invention may be made by a variety of methods, including standard chemistry. Any previously defined variable will continue to have previously defined meaning unless otherwise noted. Illustrative general synthetic methods are set out below and then specific compounds of Formula (I) are prepared in the Examples.

Compounds of general Formula (I) may be prepared by methods known in the art of organic synthesis as set forth in part by the following synthetic schemes. In all the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers. When a compound is desired as a single isomer it may be obtained by various methods of separation of the final product or key intermediate or alternatively may be made by a stereo specific synthesis using isomerically pure intermediates or methods to impart isomeric purity. These are known to those skilled in the art.

Compounds were analyzed by common methods known to those skilled in the art. NMR and HPLC and LCMS were used to evaluate isolated compounds and to evaluate reaction mixtures. LCMS conditions used water and MeCN as the two solvents using a Symmetry C18, 5 um, 4.6×50 mm column. A linear gradient was used from time 0 (10% MeCN) to time 4.5 min (95% MeCN). The flow rate was 1.7 ml/min. Evaluation was at 254 nm.

The following solvents, reagents, protecting groups, moieties, and other designations may be referred to by their abbreviations in parenthesis:

Me: methyl;
Et: ethyl;
Pr: propyl;
i-Pr: isopropyl;
Bu: butyl;
t-Bu: tert-butyl;
Ph: phenyl,
Ac: acetyl
AcOH: acetic acid
Aq.: aqueous
AUC: area under a curve
Conc.: concentrated
DMF: dimethylformamide
DMSO: dimethylsulfoxide
EtOAc: ethyl acetate
EtOH: ethyl alcohol
Ex.: Example
g: grams
h: hours
HPLC: high-performance liquid chromatography
LCMS: liquid chromatography mass spectrometry
MeOH: methyl alcohol
MS: mass spectrometry
NA: not applicable
ND: no data reported
NMR: nuclear magnetic resonance spectrometry
Ret Time: retention time
RT or rt: room temperature
Satd, Sat'd, sat'd and satd.: saturated
TFA: trifluoroacetic acid
THF: tetrahydrofuran Methods of Preparation Compounds of the invention may be prepared according to the general synthetic schemes and exemplary procedures provided herein and modifications thereof known to those of skill in the art. All documents cited are incorporated herein by reference in their entirety. Starting materials are commercially available or readily prepared by one of ordinary skill in the art.

There are currently many suppliers of chemical reagents. Examples of chemical suppliers: Sigma Aldrich, Saint Louis, Mo.; Alfa Aesar, Tewksbury, Mass.; TCI America.

Portland, Oreg.; BroadPharm, San Diego, Calif. and Cambridge BioSciences, Cambridge, UK, in no way is this list meant to be limiting.

A general synthetic scheme shown as Scheme 1 (see US 2015/023362), is a series of reactions that one skilled in the art may use to prepare compounds of the invention. Substituents X and Y denote various substituents that may be used for this reaction sequence and their positions on the molecule are not limited. In addition, this example is not to be limiting with regard to the number of substituents that may be used therein. One uses and a substituted benzaldehyde SAA and the other approach uses benzyl amine SE. Both substituted benzyl amines and substituted benzaldehydes are commercially available. Alternative reaction conditions may be employed for the various transformations in Scheme 1. As an example, but not limited by these alternative reaction conditions, alternative reaction conditions as given in US 2014/0335048 may be used. To further exemplify the chemistry, in Scheme 1, X may be $R_{22}$ and Y may be $R_1$, however this should not be limiting with regard to substituents and their positions on the rings in question.

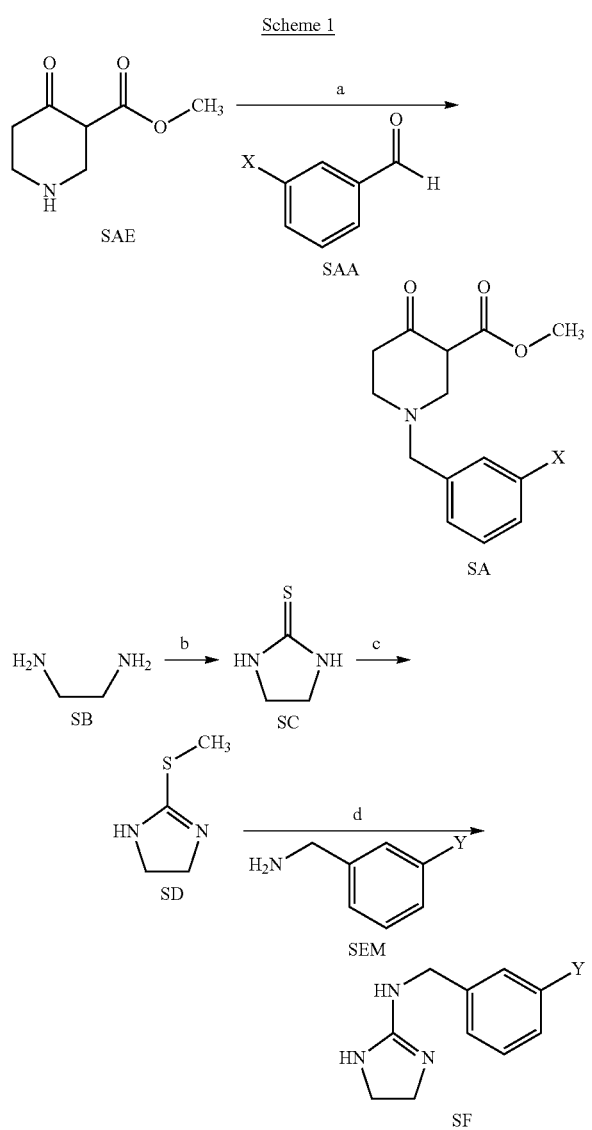

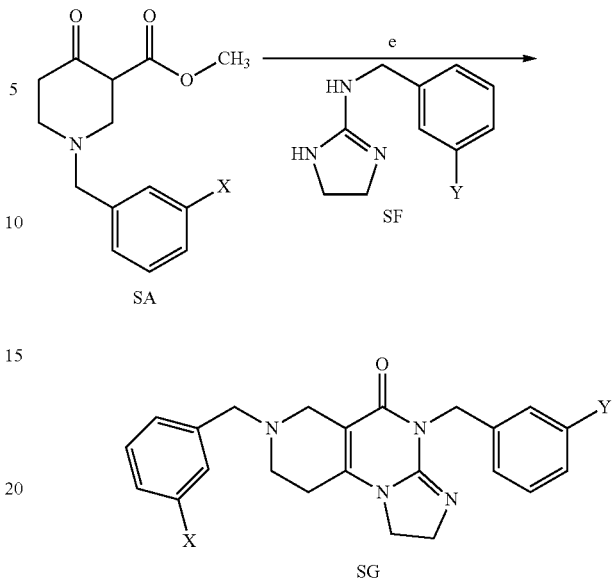

Synthesis of compounds by Scheme 1: (a) NaBH(OAc)$_3$, CH$_2$Cl$_2$, 30° C./4 h; (b) NaOH, CS$_2$, H$_2$O, 1 h, (c) MeI, MeOH/reflux 30 min, (d) dioxane/reflux 12 h (e) MeONa MeOH/reflux 12-15 h.

In Scheme 2, an alternative reaction for the formation of an analog of SF, SDD is shown. As in Scheme 1, substituents X and Y denote various substituents that may be used for this reaction sequence and their positions on the molecule are not limited. In addition, this example is not to be limiting with regard to the number of substituents that may be used therein. To further exemplify the chemistry, in Scheme 2, X may be $R_{23}$ and Y may be $R_2$, however this should not be limiting with regard to substituents and their positions on the rings in question.

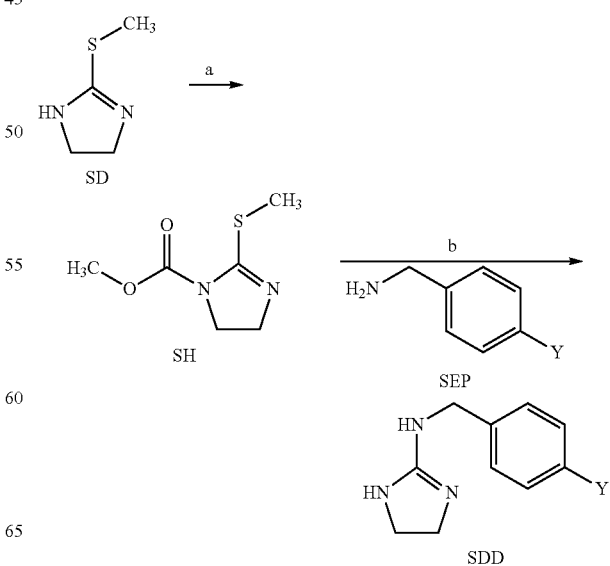

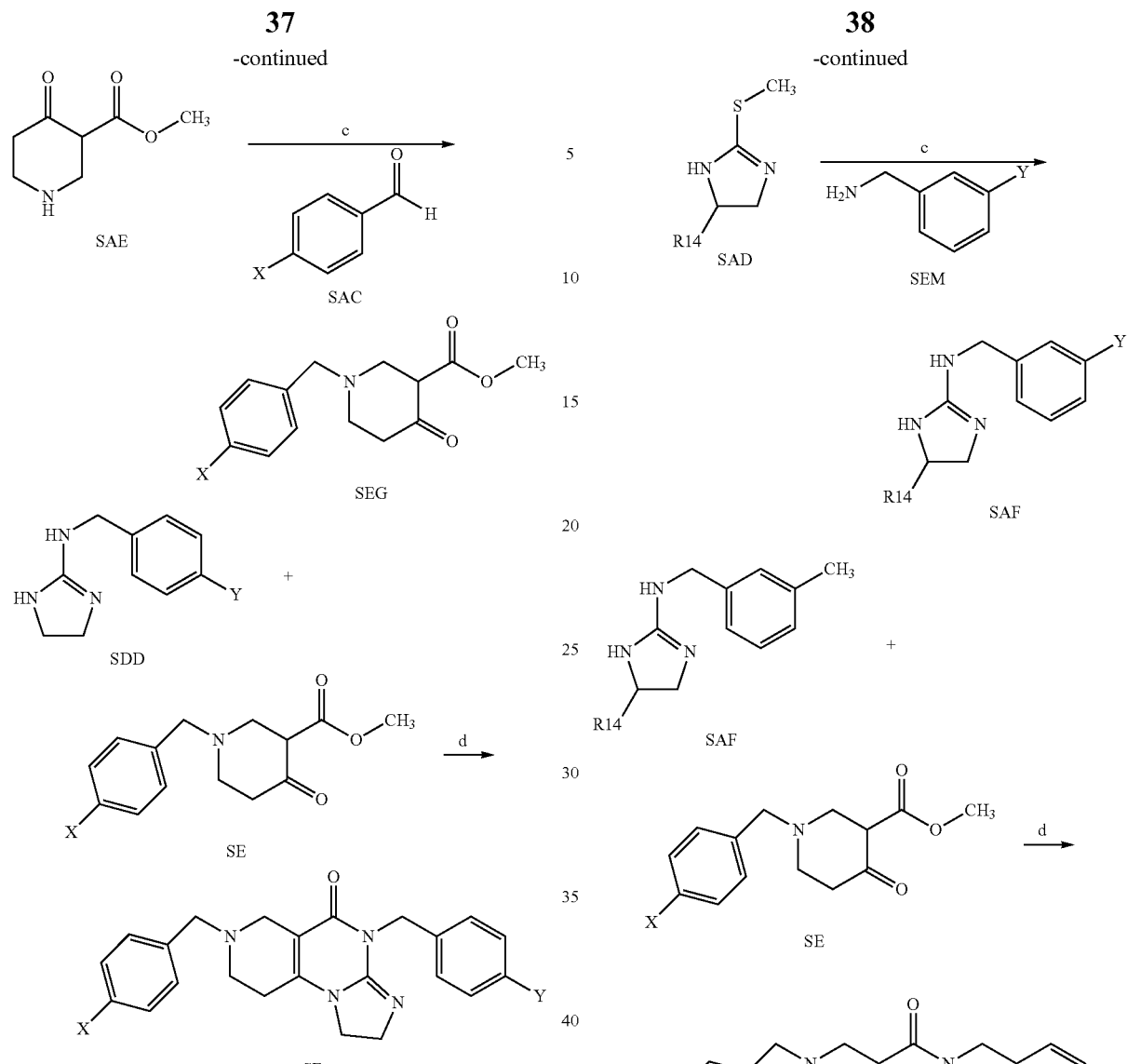

Synthesis of compounds by Scheme 2: (a) methyl chloroformate, Et₃N, CH₂Cl₂, 0° C. to rt 44 h; (b) MeOH, AcOH, reflux, 45 h; (c) NaBH(OAc)₃, CH₂Cl₂, 30° C./4 h; (d) NaOMe, MeOH, reflux, 18 h.

In Scheme 3, synthesis of analogs with substitution about $R_{14}$, $R_{15}$, $R_{16}$ and $R_{17}$ is shown. $R_{14}$ is chosen to exemplify the chemistry that may be used for this reaction sequence and is in no way meant to be limiting. The final condensation reaction shown with reaction conditions provides both SAG and SAH. That is $R_{14}$ and $R_{16}$ would be the same residue. Separation of this mixture would provide the two analogs.

Scheme 3

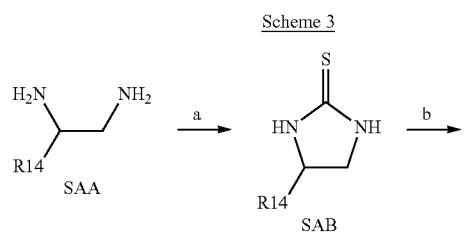

Synthesis of compounds by Scheme 3: (a) NaOH, CS₂, H₂O, 1 h, (b) MeI, MeOH/reflux 30 min, (c) dioxane/reflux 12 h (d) MeONa MeOH/reflux 12-15 h.

EXAMPLES

Example 1

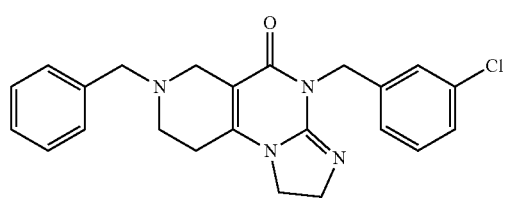

11-benzyl-7-[(3-chlorophenyl)methyl]-2,5,7,11-tetraazatricyclo[7.4.0.0^{2,6}]trideca-1(9),5-dien-8-one (1)

Synthesis of 1B

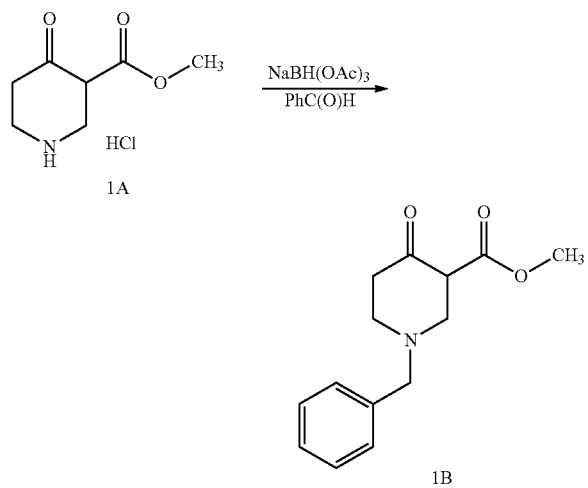

To a 50 mL three necked flask, was charged with compound 1A (1 g, 5.2 mmol), 1,2 dichloroethane (10 mL), DIEA (665 mg, 5.2 mmol). The mixture was stirred for 15 minutes at 25° C. Benzaldehyde (5.2 mmol) was added, followed by NaBH(OAc)$_3$ (6.7 mmol). The mixture was stirred for 2 hours at 25° C. LC-MS analysis confirmed that the reaction was complete. The reaction was quenched with ice water (20 mL), extracted with dichloromethane 20 mL twice. The combined organic phase was washed with saturated aqueous NaHCO$_3$, (2×25 mL) and concentrated. Compound 1B was obtained (1.22 g). The product was used for next step without further purification.

Synthesis of 1D

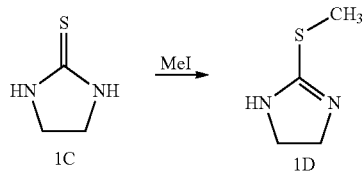

Compound 1C (59.8 mmol) was dissolved in methanol (70 mL), CH$_3$I (89.7 mmol) was added dropwise at 25° C. After refluxed for 30 minutes, the solvent was removed under vacuum. The residue was suspended in MTBE (50 mL) and filtered. The resulting solid was dried under vacuum to afford compound 1D (yield 83%) as white solid.

Synthesis of 1F

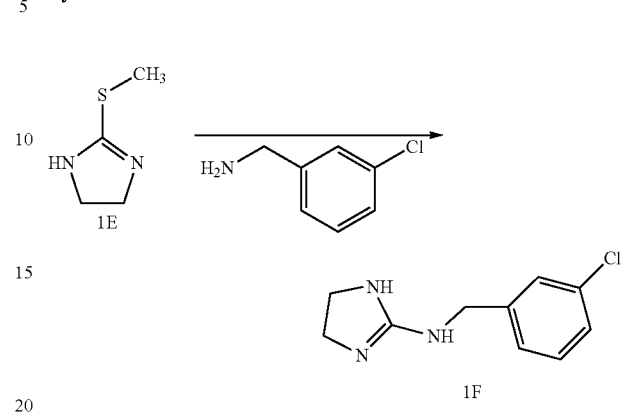

Compound 1E (2 mmol), and (3-chlorophenyl)methanamine (4.2 mmol) was dissolved in dioxane (5 mL). The mixture was refluxed for 12 hours. Analysis of the reaction mixture by LC-MS confirmed that the reaction was completed. The solvent was removed, and the residue was suspended with toluene for 12 hours. The suspension was filtered and the filtered cake was dried under vacuum to afford compound 1F.

Synthesis of 1

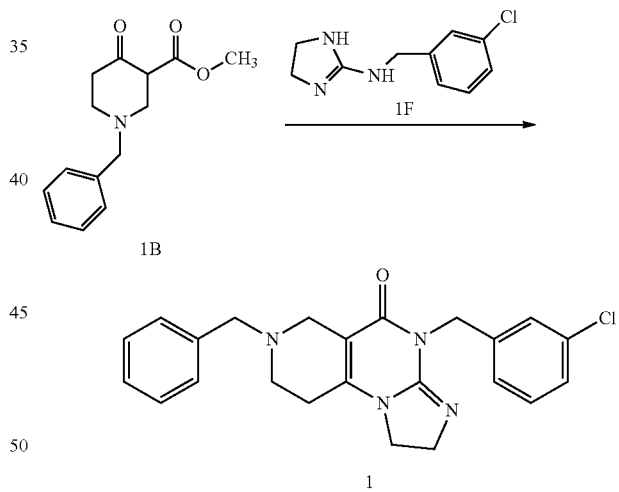

To a 10 mL three necked flask, was charged with compound 1F (0.4 mmol), compound 1B (0.4 mmol), methanol (3 mL) and MeONa (1.2 mmol). The mixture was refluxed for 15 h hours. Analysis of the reaction mixture by LC-MS confirmed that the reaction was complete. The reaction was cooled down to room temperature. Half of the solvent was removed under vacuum. Water (2 mL) was added drop wise. A brown solid precipitated, was filtered and washed with water. The solid was dried under vacuum to afford compound 1 (yield 25%).

$^1$HNMR (400 MHz, CDCl$_3$) δ 2.44 (s, 2H), 2.65 (t, J=6.4 Hz, 2H), 3.29 (s, 2H), 3.65 (s, 2H), 3.87 (s, 4H), 5.01 (s, 2H), 7.19-7.42 (m, 9H); LC-MS: m/z=406.7 (M+1).

Example 2

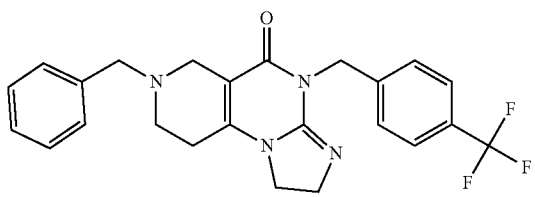

11-benzyl-7-{[4-trifluoromethyl)phenyl]methyl}-2,5,7,11-tetraazatricyclo[7.4.0.0$^{2,6}$]trideca-1(9), 5-dien-8-one (2)

The procedure to prepare Compound 2 is same as Example 1 except in step 3, (3-chlorophenyl)methanamine is replaced by [4-(trifluoromethyl)phenyl]methanamine. Yield 18%; $^1$HNMR (400 MHz, CD$_3$OD), δ 2.61 (t, J=4.0 Hz, 2H), 2.76 (t, J=4.0 Hz, 2H), 3.24 (s, 2H), 3.72 (s, 2H), 3.86 (t, J=6.4 Hz, 2H), 4.05 (t, J=6.4 Hz, 2H), 5.10 (s, 2H), 7.28-7.39 (m, 5H), 7.50 (d, J=5.2 Hz, 2H), 7.60 (d, J=5.2 Hz, 2H); LC-MS: m/z=441.2 (M+1).

Example 3

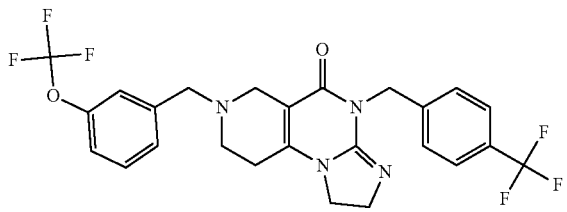

11-benzyl-7-{[3-(trifluoromethyloxy)phenyl]methyl}-7-{[4-(trifluoromethyl)phenyl}-2,5,7,11-tetraazatricyclo[7.4.0.0$^{2,6}$]trideca-1(9), 5-dien-8-one (3)

Compound 3 prepared similarly as Example 1. Yield 30%; $^1$HNMR (400 MHz, CD$_3$OD) δ 2.63 (t, J=5.6 Hz, 2H), 2.76 (t, J=5.6 Hz, 2H), 3.25 (s, 2H), 3.75 (s, 2H), 3.83-3.88 (m, 2H), 4.03-4.07 (m, 2H), 5.1 (s, 2H), 7.20 (d, J=8 Hz, 1H), 7.32-7.51 (m, 5H), 7.59 (d, J=8.4 Hz, 2H); LC-MS: m/z=524.7 (M+1).

Example 4

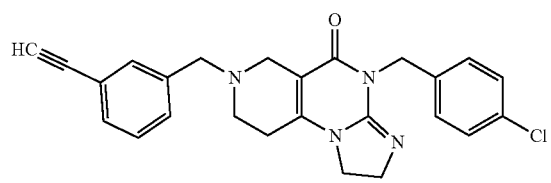

7-[(4-chlorophenyl)methyl]-11-[(3-ethynylphenyl)-2,5,7,11-tetraazatricyclo[7.4.0.0$^{2,6}$]trideca-1(9), 5-dien-8-one (4)

Compound 4 is prepared in a similar fashion as Example 1. Yield 30%; $^1$HNMR (400 MHz, DMSO-d6) δ 2.51 (s, 2H), 2.62 (s, 2H), 3.02 (s, 2H), 3.61 (s, 2H), 3.7 (t, J=8.8 Hz, 2H), 3.94 (d, J=9.2 Hz, 2H), 4.19 (s, 1H), 4.88 (s, 2H), 7.3-7.42 (m, 8H); LC-MS: m/z=430.8 (M+1).

Example 5

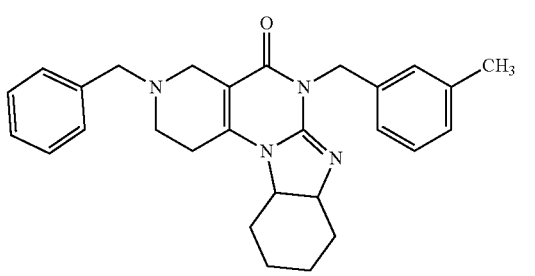

5-benzyl-9-[(3-methylphenyl)methyl]-1,5,9,11-tetraazatetracyclo[8.7.0.0$^{2,7}$.0$^{12,17}$]heptadeca-2(7), 10-dien-8-one (5)

Compound 5 is prepared in a similar fashion as Example 1. The procedure is given below.

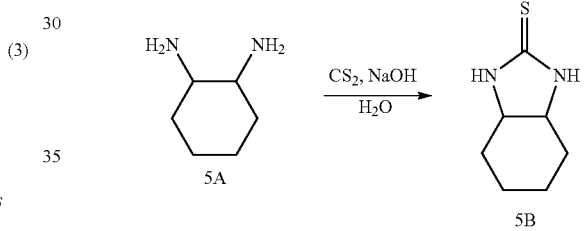

Synthesis of 5B

To a well-stirred solution of cyclohexane-1,2-diamine (11.4 g, 0.1 mol) in water was added sodium hydroxide (8 g, 0.2 mmol) followed by carbon disulfide (8.36 g, 0.11 mmol) at room temperature. The mixture was heated to 100° C. overnight. The mixture was cooled, acidified with dilute hydrochloric acid, and extracted into DCM (100 ml×3 mL). The combined organic layer was dried over sodium sulfate, and the solvent was removed completely to give the product 5B an off-white solid (12.7 g yield, 81%). $^1$H-NMR (400 MHz, CDCl$_3$): δ1.12-1.31 (m, 2H), 1.33-1.52 (m, 2H), 1.57-1.91 (m, 2H), 1.99-2.08 (m, 2H), 3.26-3.35 (m, 2H), 6.62 (s, 1H) MS (CI): 157.2 (M+1).

5.2 Synthesis of 5C

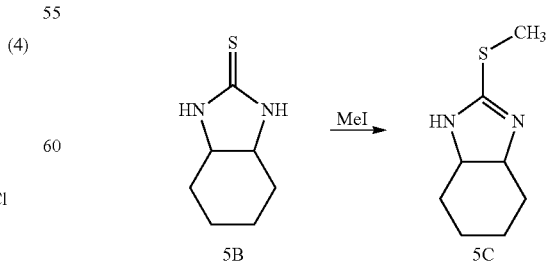

Compound 5B (12.5 g, 80.12 mmol) was dissolved in MeOH (250 ml) and MeI (17.1 g, 120.2 mmol) was added.

The resulting mixture was refluxed for 2 h. The volatiles were removed under reduced pressure yielding 5C, (13.5 g Yield: 99%) as off-white solid that was used without further purification.
Synthesis of 5D

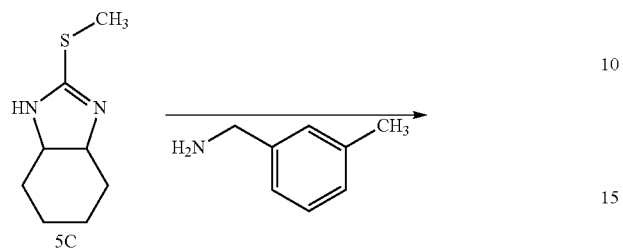

5C

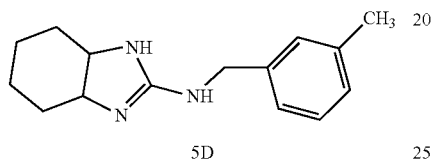

5D

Compound 5C (1 g, 5.9 mmol) was dissolved in t-BuOH (15 ml) and 3-methylbenzylamine (14.3 g, 11.8 mmol) was added. The mixture was refluxed for 5 h. The volatiles were evaporated under reduced pressure and the oily residue was suspended in H₂O, alkalized with 1 N NaOH and extracted with DCM (20 m×4). The combined organic phase was dried over MgSO₄ and evaporated under reduced pressure. The crude residue of 5D was purified by column chromatography on silica gel using DCM/MeOH (10/1) as eluent to yield 5D (810 mg yield: 60%) as yellow solid.
Synthesis of 5

Compound 5C (810 mg, 3.33 mmol) and compound 1B (825 mg, 3.33 mmol) were dissolved in MeOH (10 ml) and MeONa (382 mg, 7.08 mmol) was added. The resulting mixture was refluxed overnight. The crude residue was purified by preparative-HPLC to give 5 (219 mg, yield 15%). ¹H-NMR (400 MHz, CD₃OD) δ 1.33-1.76 (m, 7H), 1.92-1.99 (m, 2H), 2.29 (s, 3H), 2.59-2.69 (m, 2H), 2.76-2.82 (m, 1H), 3.11-3.14 (m, 1H), 3.31-3.37 (m, 1H), 3.67 (s, 2H), 3.9 (s, 1H), 4.30-4.36 (m, 1H), 4.98-5.09 (m, 2H), 7.03-7.37 (m, 9H); LC-MS: m/z=440.9 (M+1).

Example 6

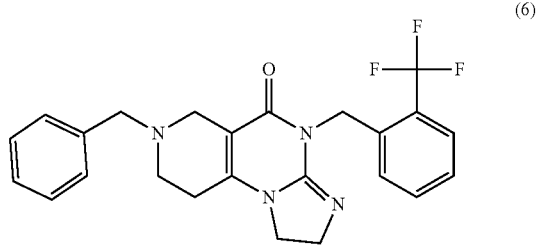

(6)

7-benzyl-4-(2-(trifluoromethyl)benzyl)-1,2,6,7,8,9-hexahydroimidazo[1-2-a]pyrido[3,4-e]pyrimidin-5(4H)-one (6)

It is prepared similarly as example 1. Yield 30%; ¹HNMR (400 MHz, CDCl₃) δ 2.54 (s, 2H), 2.71 (s, 2H), 3.32 (s, 2H), 3.68 (s, 2H), 3.85-3.97 (m, 4H), 5.30 (s, 2H), 7.10 (d, J=7.6 Hz, 1H), 7.28-7.33 (m, 6H), 7.43 (t, J=7.6 Hz, 1H), 7.63 (d, J=7.6 Hz, 1H); LC-MS: m/z=441.2 (M+1).

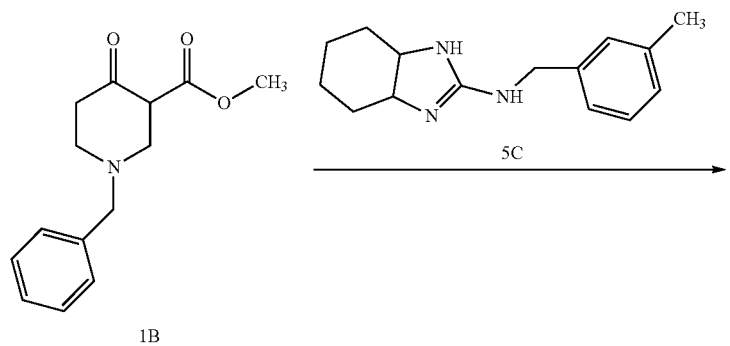

1B                                      5C

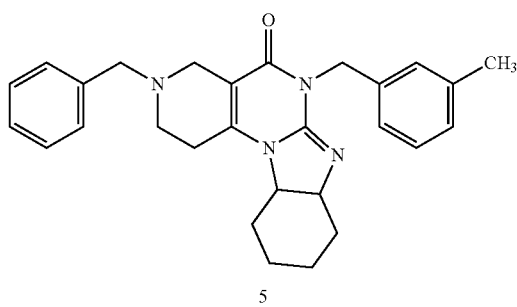

5

Example 7

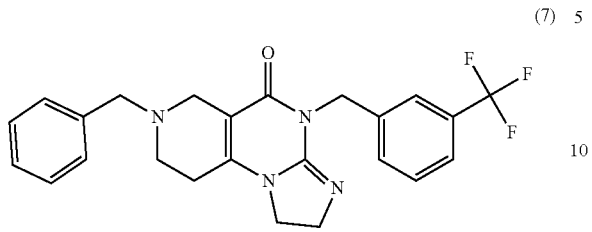

7-benzyl-4-(3-trifluoromethyl)benzyl)-1,2,6,7,8,9-hexahydroimidazo[1,2-a]pyrido[3,4-e]pyrimidin-5(4H)-one (7)

It is prepared similarly as example 1. Yield 30%; $^1$HNMR (400 MHz, CD$_3$OD) δ 2.55 (t, J=3.6 Hz, 2H), 2.71 (t, J=4 Hz, 2H), 3.23 (s, 2H), 3.68 (s, 2H), 3.84 (t, J=6.4 Hz, 2H), 3.99 (t, J=6.4 Hz, 2H), 5.07 (s, 2H), 7.27 (t, J=4.4 Hz, 1H), 7.32-7.37 (m, 4H), 7.47 (t, J=5.2 Hz, 1H), 7.54 (d, J=5.2 Hz, 1H), 7.61 (d, J=5.6 Hz, 1H), 7.68 (s, 1H); LC-MS: m/z=441.2 (M+1).

Example 8

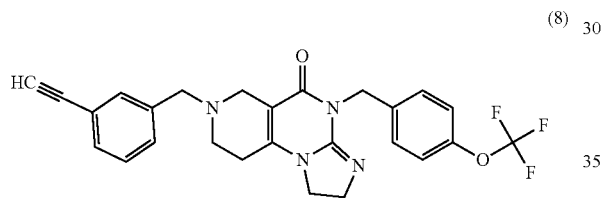

7-(3-ethynylbenzyl)-4-(4-(trifluoromethoxy)benzyl)-1,2,6,7,8,9-hexahydroimidazo[1,2-a]pyrido[3,4-e]pyrimidin-5(4H)-one (8)

It is prepared similarly as example 1. Yield 20%; $^1$HNMR (400 MHz, CDCl$_3$) δ 2.46 (s, 2H), 2.65 (t, J=5.2 Hz, 2H), 3.07 (s, 1H), 3.28 (s, 2H), 3.63 (s, 2H), 3.89 (s, 4H), 5.04 (s, 2H), 7.11-7.13 (d, J=8 Hz, 2H), 7.27-7.32 (m, 2H), 7.38-7.4 (d, J=8 Hz, 1H), 7.49 (t, 8 Hz, 3H); LC-MS: m/z=480.8 (M).

Example 9

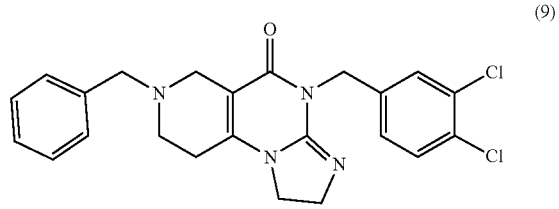

7-benzyl-4-(3,4-dichlorobenzyl)-1,2,6,7,8,9-hexahydroimidazo[1,2-a]pyrido[3,4-e]pyrimidin-5(4H)-one (9)

It is prepared similarly as example 1. Yield 30%; $^1$HNMR (400 MHz, CD$_3$OD) δ 2.59 (t, J=5.6 Hz, 2H), 2.74 (t, J=5.6 Hz, 2H), 3.23 (s, 2H), 3.7-3.71 (d, J=4 Hz, 2H), 3.86 (t, J=9.2 Hz, 2H), 4.03 (t, J=9.6 Hz, 2H), 4.97 (s, 2H), 7.27-7.55 (m, 8H); LC-MS: m/z=441.3 (M+1).

Example 10

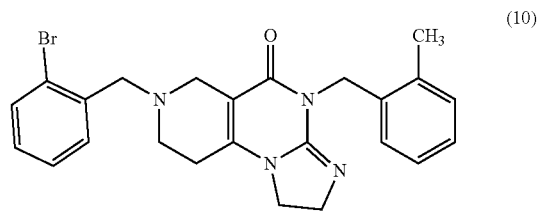

7-(2-bromobenzyl)-4-(2-methylbenzyl)-1,2,6,7,8,9-hexahydroimidazo[1,2-a]pyrido[3,4-e]pyrimidin-5(4H)-one (10)

It is prepared similarly as example 1. Yield 30%; $^1$HNMR (400 MHz, CD$_3$OD) δ 2.38 (s, 3H), 2.61 (s, 2H), 2.81 (t, J=4.8 Hz, 2H), 3.31 (s, 2H), 3.8 (t, J=8.4 Hz, 4H), 4.02 (t, J=9.2 Hz, 2H), 5.01 (s, 2H), 6.89-6.91 (d, J=8 Hz, 1H), 7.05-7.2 (m, 4H), 7.34 (t, J=7.6 Hz, 1H), 7.51-7.53 (d, J=8 Hz, 1H), 7.58-7.6 (d, J=8 Hz, 1H); LC-MS: m/z=465.2 (M+1).

Example 11

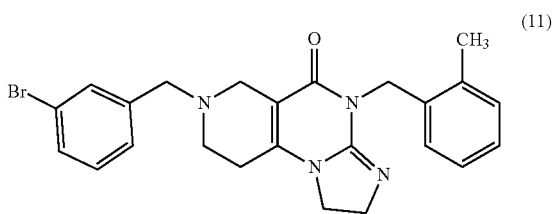

7-(3-bromobenzyl)-4-(2-methylbenzyl)-1,2,6,7,8,9-hexahydroimidazo[1,2-a]pyrido[3,4-e]pyrimidin-5(4H)-one (11)

It is prepared similarly as example 1. Yield 30%; $^1$HNMR (400 MHz, DMSO_d6) δ 2.32 (s, 3H), 2.57 (s, 2H), 2.66 (t, J=4.8 Hz, 2H), 3.06 (s, 2H), 3.64-6.7 (m, 4H), 3.97 (t, J=9.2 Hz, 2H), 4.87 (s, 2H), 6.88-6.9 (d, J=8 Hz, 1H), 7.09-7.14 (m, 3H), 7.3-7.35 (m, 2H), 7.45-7.47 (d, J=8 Hz, 1H), 7.53 (s, 1H); LC-MS: m/z=465.2 (M+1).

Example 12

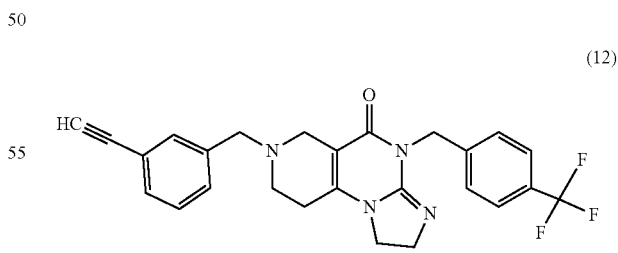

7-(3-Ethynylbenzyl)-4-(4-(trifluoromethoxy)benzyl)-1,2,6,7,8,9-hexahydroimidazo[1,2-a]pyrido[3,4-e]pyrimidin-5(4H)-one (12)

It is prepared similarly as example 1. Yield 20%; $^1$HNMR (400 MHz, CDCl$_3$) δ 2.48 (d, J=5.6 Hz, 2H), 2.66 (t, 5.2 Hz, 2H), 3.06 (s, 1H), 3.29 (s, 2H), 3.64 (s, 2H), 3.91 (s, 4H), 5.1 (s, 2H), 7.27-7.33 (m, 2H), 7.4 (d, J=7.2 Hz, 1H), 7.48 (s, 1H), 7.52-7.57 (m, 4H); LC-MS: m/z=464.8 (M+1).

Example 13

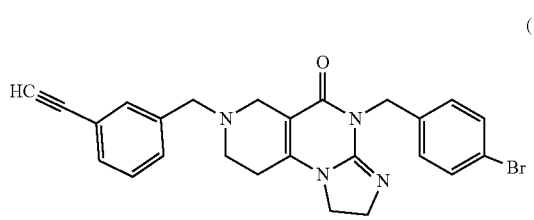

4-(4-Bromobenzyl)-7-(3-ethynylbenzyl)-1,2,6,7,8,9-hexahydroimidazo[1,2-a]pyrido[3,4-e]pyrimidin-5(4H)-one (13)

It is prepared similarly as example 1. Yield 30%; $^1$HNMR (400 MHz, CDCl$_3$) δ 2.46 (t, J=5.6 Hz, 2H), 2.65 (t, J=5.6 Hz, 2H), 3.06 (s, 1H), 3.28 (s, 2H), 3.64 (s, 2H), 3.89 (s, 4H), 5.0 (s, 2H), 7.27-7.42 (m, 7H), 7.48 (s, 1H); LC-MS: m/z=476.7 (M+1).

Example 14

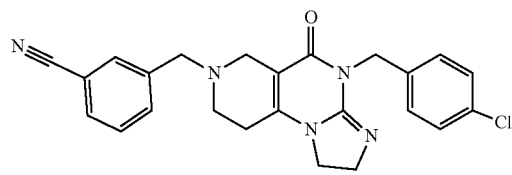

3-((4-(4-Chlorobenzyl)-5-oxo-1,2,4,5,8,9-hexahydroimidazo[1,2-a]pyrido[3,4-e]pyrimidin-7(6H)-yl)methyl)benzonitrile (14)

It is prepared similarly as example 1. Yield 25%; $^1$HNMR (400 MHz, CDCl$_3$) δ 2.49 (t, J=5.6 Hz, 2H), 2.68 (t, J=5.6 Hz, 2H), 3.26 (s, 2H), 3.68 (s, 2H), 3.91 (s, 4H), 5.0 (s, 2H), 7.25 (t, J=5.6 Hz, 2H), 7.42 (t, J=8 Hz, 3H), 7.55-7.57 (d, J=8 Hz, 2H), 7.66 (s, 1H); LC-MS: m/z=432.2 (M+1).

Example 15

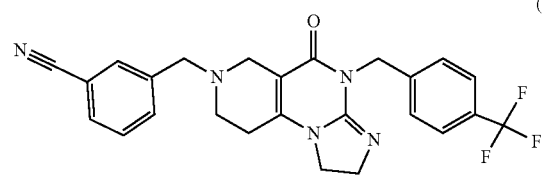

3-((5-Oxo-4-(4-(trifluoromethyl)benzyl)-1,2,4,5,8,9-hexahydroimidazo[1,2-a]pyrido[3,4e]pyrimidin-7(6H)-yl)methyl)benzonitrile (15)

It is prepared similarly as example 1. Yield 22%; $^1$HNMR (400 MHz, CDCl$_3$) δ 2.5 (s, 2H), 2.69 (t, J=5.6 Hz, 2H), 3.27 (s, 2H), 3.69 (s, 2H), 3.92 (s, 4H), 5.1 (s, 2H), 7.43 (t, J=8 Hz, 1H), 7.52-7.57 (m, 6H), 7.66 (s, 1H); LC-MS: m/z=466.1 (M+1).

Example 16

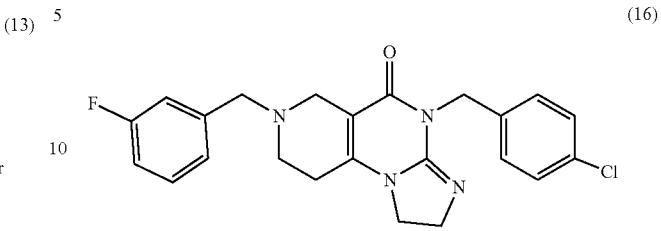

4-(4-Chlorobenzyl)-7-(3-fluorobenzyl)-1,2,6,7,8,9-hexahydroimidazo[1,2-a]pyrido[3,4-e]pyrimidin-5(4H)-one (16)

It is prepared similarly as example 1. Yield 25%; $^1$HNMR (400 MHz, CDCl$_3$) δ 2.46 (t, J=5.6 Hz, 2H), 2.65 (t, J=5.6 Hz, 2H), 3.27 (s, 2H), 3.64 (s, 2H), 3.89 (s, 4H), 5.0 (s, 2H), 6.92-6.97 (m, 1H), 7.07 (t, J=7.6 Hz, 2H), 7.23-7.29 (m, 3H), 7.4-7.42 (d, J=8 Hz, 2H); LC-MS: m/z=425.2 (M+1).

Example 17

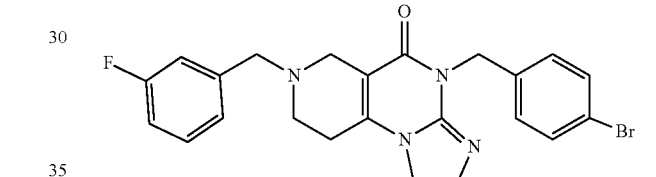

4-(4-Bromobenzyl)-7-(3-fluorobenzyl)-1,2,6,7,8,9-hexahydroimidazo[1,2-a]pyrido[3,4-e]pyrimidin-5(4H)-one (17)

It is prepared similarly as example 1. Yield 30%; $^1$HNMR (400 MHz, CDCl$_3$) δ2.47 (t, J=5.6 Hz, 2H), 2.65 (t, J=5.6 Hz, 2H), 3.27 (s, 2H), 3.65 (s, 2H), 3.89 (s, 4H), 4.99 (s, 2H), 6.93-6.97 (m, 1H), 7.05-7.09 (m, 2H), 7.24-7.29 (m, 1H), 7.33-7.41 (m, 4H); LC-MS: m/z=471.1 (M+1).

Example 18

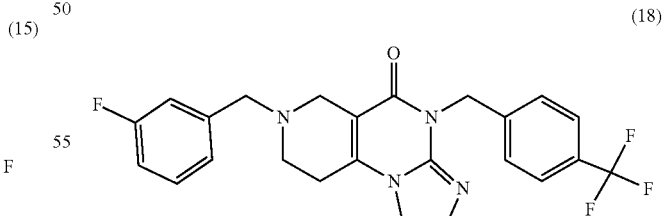

7-(3-Fluorobenzyl)-4-(4-trifluoromethyl)benzyl)-1,2,6,7,8,9-hexahydroimidazo[1,2-a]pyrido[3,4-e]pyrimidin-5(4H)-one (18)

It is prepared similarly as example 1. Yield 25%; $^1$HNMR (400 MHz, CDCl$_3$) δ2.48 (t, J=5.6 Hz, 2H), 2.67 (t, J=5.6 Hz, 2H), 3.28 (s, 2H), 3.65 (s, 2H), 3.91 (s, 4H), 5.1 (s, 2H), 6.93-6.98 (m, 1H), 7.08 (t, J=7.6 Hz, 2H), 7.26-7.3 (m, 1H), 7.52-7.57 (m, 4H); LC-MS: m/z=459.2 (M+1).

Example 19

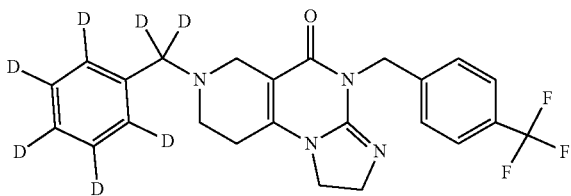

7-(3-Perdeuteriobenzyl)-4-(4-(trifluoromethyl)benzyl)-1,2,6,7,8,9-hexahydroimidazo[1,2-a]pyrido[3,4-e]pyrimidin-5(4H)-one (19)

It is prepared similarly as example 1. Yield 30%; $^1$HNMR (400 MHz, CDCl$_3$) δ 2.46 (s, 2H), 2.66 (s, 2H), 3.3 (s, 2H), 3.89 (s, 4H), 5.09 (s, 2H), 7.54 (s, 4H); LC-MS: m/z=448.3 (M+1).

Example 20

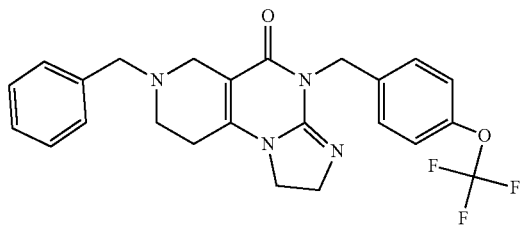

7-benzyl-4-(4-trifluoromethyl)benzyl)-1,2,6,7,8,9-hexahydroimidazo[1,2-a]pyrido[3,4-e]pyrimidin-5(4H)-one (20)

It is prepared similarly as example 1. Yield 30%; $^1$HNMR (400 MHz, CDCl$_3$) δ 2.43 (t, J=5.6 Hz, 2H), 2.64 (t, J=5.6 Hz, 2H), 3.28 (s, 2H), 3.65 (s, 2H), 3.85-3.88 (m, 4H), 5.03 (s, 2H), 7.1-7.12 (d, J=8 Hz, 2H), 7.25-7.31 (m, 5H), 7.49-7.51 (d, J=8 Hz, 2H); LC-MS: m/z=456.8 (M).

Example 21

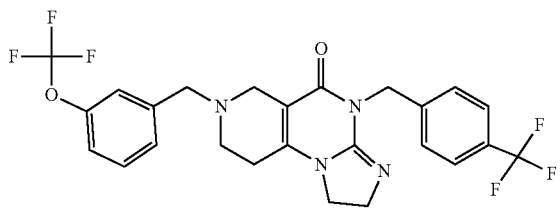

7-(3-trifluoromethoxy)benzyl)-4-(4-trifluoromethyl)benzyl)-1,2,6,7,8,9-hexahydroimidazo[1,2-a]pyrido[3,4-e]pyrimidin-5(4H)-one (21)

It is prepared similarly as example 1. Yield 25%; $^1$HNMR (400 MHz, CD$_3$OD) δ 2.63 (t, J=5.6 Hz, 2H), 2.76 (t, J=5.6 Hz, 2H), 3.25 (s, 2H), 3.75 (s, 2H), 3.83-3.88 (m, 2H), 4.03-4.07 (m, 2H), 5.1 (s, 2H), 7.20 (d, J=8 Hz, 1H), 7.32-7.51 (m, 5H), 7.59 (d, J=8 Hz, 2H); LC-MS: m/z=524.7 (M).

Example 22

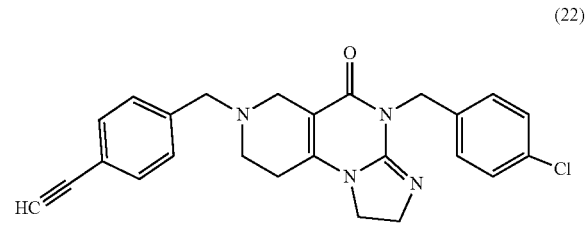

4-(4-chlorobenzyl)-7-(4-ethynylbenzyl)-1,2,6,7,8,9-hexahydroimidazo[1,2-a]pyrido[3,4-e]pyrimidin-5(4H)-one (22)

It is prepared similarly as example 1. Yield 25%; $^1$HNMR (400 MHz, DMSO_d6) δ 2.51 (s, 2H), 2.62 (t, J=5.6 Hz, 2H), 3.02 (s, 2H), 3.62 (s, 2H), 3.71 (t, J=9.2 Hz, 2H), 3.93 (t, J=9.2 Hz), 4.88 (s, 2H), 7.3-7.36 (m, 6H), 7.43-7.45 (d, J=8 Hz, 2H); LC-MS: m/z=430.8 (M).

Example 23

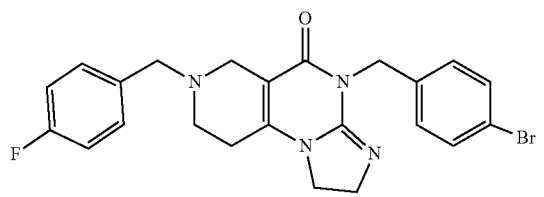

4-(4-chlorobenzyl)-7-(4-ethynylbenzyl)-1,2,6,7,8,9-hexahydroimidazo[1,2-a]pyrido[3,4-e]pyrimidin-5(4H)-one (23)

It is prepared similarly as example 1. Yield 30%; $^1$HNMR (400 MHz, CDCl$_3$) δ 2.46 (t, J=5.6 Hz, 2H), 2.65 (t, J=5.6 Hz, 2H), 3.26 (s, 2H), 3.62 (s, 2H), 3.89 (s, 4H), 4.99 (s, 2H), 6.98 (t, J=8.8 Hz, 2H), 7.27-7.3 (m, 2H), 7.33-7.41 (m, 4H); LC-MS: m/z=471.1 (M+1).

Example 24

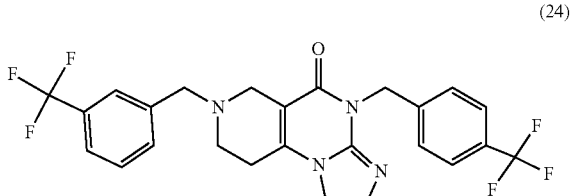

7-(3-Trifluoromethyl)benzyl)-4-(4-trifluoromethyl)benzyl)-1,2,6,7,8,9-hexahydroimidazo[1,2-a]pyrido[3,4-e]pyrimidin-5(4H)-one (24)

It is prepared similarly as example 1. Yield 25%; $^1$HNMR (400 MHz, CDCl$_3$) δ2.48 (t, J=5.6 Hz, 2H), 2.67 (t, J=5.6

Hz, 2H), 3.29 (s, 2H), 3.71 (s, 2H), 3.9 (s, 4H), 5.1 (s, 2H), 7.43 (t, J=7.6 Hz, 1H), 7.51-7.57 (m, 6H), 7.61 (s, 1H); LC-MS: m/z=509.6 (M+1).

Example 25

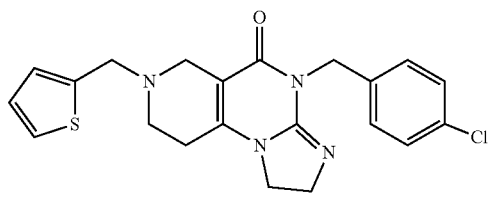

(25)

4-(4-chlorobenzyl)-7-(thiophen-2-ylmethyl)-1,2,6,7,8,9-hexahydroimidazo[1,2-a]pyrido[3,4-e]pyrimidin-5(4H)-one (25)

It is prepared similarly as example 1. Yield 25%; $^1$HNMR (400 MHz, CDCl$_3$) δ 2.47 (s, 2H), 2.66 (t, J=5.2 Hz, 2H), 3.3 (s, 2H), 3.7 (t, J=8.8 Hz, 2H), 3.89 (s, 4H), 5.01 (s, 2H), 7.05-7.07 (d, J=8 Hz, 1H), 7.15 (s, 1H), 7.23-7.28 (m, 3H), 7.4-7.42 (d, J=8 Hz, 2H); LC-MS: m/z=413.1 (M+1).

Example 26

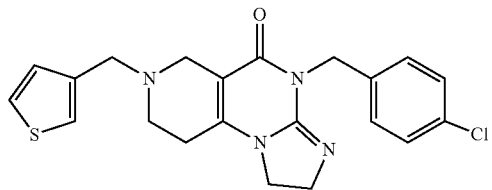

(26)

4-(4-chlorobenzyl)-7-(thiophen-3-ylmethyl)-1,2,6,7,8,9-hexahydroimidazo[1,2-a]pyrido[3,4-e]pyrimidin-5(4H)-one (26)

It is prepared similarly as example 1. Yield 25%; $^1$HNMR (400 MHz, DMSO_d6) δ 2.51 (s, 2H), 2.65 (t, J=5.2 Hz, 2H), 3.09 (s, 2H), 3.71 (t, J=8.8 Hz, 2H), 3.83 (s, 2H), 3.94 (t, J=8.8 Hz, 2H), 4.88 (s, 2H), 6.96-6.99 (m, 2H), 7.3-7.36 (m, 4H), 7.43-7.44 (d, J=4 Hz, 1H); LC-MS: m/z=413.1 (M+1).

Example 27

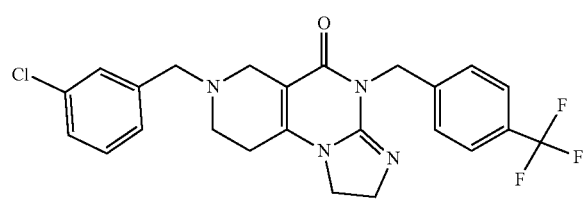

(27)

3-((1-ethyl-2,4-dioxo-3-)4-(trifluoromethyl)benzyl)-1,2,3,4,7,8-hexahydropyrido[4,3-d]pyrimidin-6(5H)-yl)methyl)benzonitrile (27)

Compound 27 was prepared as shown in Example 2 and Example 3. Notably, methyl iodide is replaced by iodoethane. Yield 15%; $^1$HNMR (400 MHz, CDCl$_3$) δ 1.27 (t, J=5.6 Hz, 3H), 2.68-2.74 (m, 4H), 3.34 (s, 2H), 3.7 (s, 2H), 3.86-3.91 (m, 2H), 5.16 (s, 2H), 7.44 (t, J=8 Hz, 1H), 7.52-7.58 (m, 6H), 7.67 (s, 1H); LC-MS: m/z=469.1 (M+1).

Biological Assays and Data

Compounds of the present invention may be tested on human derived cancer cells.

Cancer cell lines, HCT116 (human colon cancer) or MDA-MB-231 (MDA 231, human breast adenocarcinoma) were dispensed in 100 ul of cell suspension in a 96-well plate. The plate was incubated for 24 hours in a humidified incubator (37° C., 5% CO$_2$). The compound from the present invention, at the appropriate test concentrations, are added to the culture media of the plate. The plate is incubated for 48 hours. CCK-8 (10 ul, see below) is added to each well. The plate is incubated from 1-4 h under conditions as described above, and the absorbance at 450 nm and 650 nm is measured with a plate reader.

Cell Counting Kit-8 (CCK-8) allows sensitive colorimetric assays for the determination of the number of viable cells in the proliferation and cytotoxicity assays. Cell Counting was by CCK-8 using WST-8 (2-(2-methoxy-4-nitrophenyl)-3-(4-nitrophenyl)-5-(2,4-disulfophenyl)-2H-tetrazolium, monosodium salt), which produces a water-soluble formazan dye upon bioreduction in the presence of an electron carrier, 1-Methoxy PMS. CCK-8 solution is added directly to the cells. WST-8 is bioreduced by cellular dehydrogenases to an orange formazan product that is soluble in tissue culture medium. The amount of formazan produced is directly proportional to the number of living cells.

Biological activity on human cancer cells for selected examples is provided in Table 1. Compounds of the invention show significant and unanticipated improvements in potency on human cancer lines in comparison to TIC10 (11-benzyl-7-[(2-methylphenyl)methyl]-2,5,7,11-tetraazatricyclo[7.4.0.0$^{2,6}$]trideca-1 (9),5-dien-8-one).

TABLE 1

Biological activity data on human cancer cells for select analogs

| Compound # | IC$_{50}$ (uM, HCT116) | IC$_{50}$ (uM, MDA 231) |
|---|---|---|
| TIC10 | 2.8 | 3.0 |
| 2 | 0.03 | 0.05 |
| 3 | 0.36 | 0.27 |
| 4 | 0.082 | 0.069 |
| 5 | 1.3 | 0.069 |
| 6 | 1.4 | 1.2 |
| 7 | 0.24 | 0.40 |
| 8 | 1.8 | 0.88 |
| 9 | 0.080 | 0.120 |
| 10 | >25 | >25 |
| 11 | 0.72 | 0.74 |
| 12 | 0.22 | 0.22 |
| 13 | 0.28 | 0.28 |
| 14 | 0.011 | 0.024 |
| 15 | 0.007 | 0.024 |
| 16 | 0.028 | 0.070 |
| 17 | 0.023 | 0.064 |
| 18 | 0.022 | 0.078 |
| 19 | 0.089 | ND |
| 20 | 0.37 | 0.82 |
| 21 | 0.37 | 0.27 |

TABLE 1-continued

Biological activity data on human cancer cells for select analogs

| Compound # | IC$_{50}$ (uM, HCT116) | IC$_{50}$ (uM, MDA 231) |
|---|---|---|
| 22 | 1.8 | 3.4 |
| 23 | 0.36 | 0.61 |
| 24 | 0.087 | 0.22 |
| 25 | 1.7 | 0.71 |
| 26 | 0.57 | 0.31 |
| 27 | 0.016 | 0.016 |

In a similar fashion as the cancer evaluations given above, TIC10 and compounds 2 and 4 were examined on A549 (adenocarcinomic human alveolar basal epithelial cells). FIG. 1 shows IC$_{50}$ determinations for TIC10, compound 2 and compound 4 after 3 day (72 hour treatment). FIG. 2 shows western blots for tes compound on A549 cells after 72 hours. The following kinases were examined: Akt, pAkt, Mek1, Mek2, Erk2, pErk2 and c-Myc. In addition, Induced myeloid leukemia cell differentiation protein (Mcl-1) was also evaluated. Of particular note, is the reduction in the kinase pAkt (phosphorylated form of Akt) with compound 2 at significantly lower concentrations than TIC10. Compound 2 at 0.037 uM provides similar reductions in pAkt as does 10 uM of TIC10.

Select compounds of this invention were examined in vivo to assess pharmacokinetic properties in a mouse. TIC10 was compared to Example 4, Example 18, Example 19 and Example 26. Each compound was formulated and administered to a mouse. Blood was taken at specific time points (0.25 h, 0.5 h, 1 h, 2 h, 4 h, 8 h, and 24 h) and evaluated for the drug administered by LC/MS. Each compound was administered i.v. at 2 mg/kg and also evaluated by oral administration (gavage) at 10 mg/kg (Formulation: 5% DMSO+95% HP-β-CD (20%, W/V) yielding a solution). The select data from these studies is shown in Table 2.4 Note: In the field of pharmacokinetics, the area under the curve (AUC) is the area under the curve (mathematically known as the definite integral) in a plot of drug concentration in blood plasma vs. time. In addition, percent oral bioavailability or % F is a measure of the percent of the drug given orally that is in systemic circulation in the plasma. See U.S. Pat. No. 9,676,760 and references cited therein.

TABLE 2

Evaluation of TIC10, Example 4, Example 18, Example 19 and Example 27 in a mouse

| Compound Evaluated | AUC(0-infinity) [h*ng/mL] 10 mg/kg oral | Oral Bioavailability (% F) |
|---|---|---|
| TIC10 | 3.1 | 1.2 |
| Ex. 4 | 255 | 33 |
| Ex. 18 | 823 | 27 |
| Ex. 19 | 604 | 60 |
| Ex. 27 | 449 | 14 |

All publications and patent applications cited in the specification are herein incorporated by reference in their entirety. Although the foregoing invention has been described in some detail by way of illustration and example, it will be readily apparent to those of ordinary skill in the art in light of the teachings of this invention that certain changes and modifications may be made thereto without departing from the spirit or scope of the appended claims.

What is claimed is:

1. A compound of Formula (I):

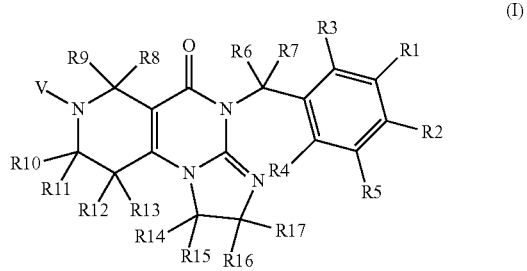

wherein

R$_1$ and R$_2$ are independently selected from the group consisting of hydrogen, —F, —Cl, —Br, —I, —CN, (C1-C3)haloalkoxy, (C1-C4)alkoxy, (C1-C6) alkyl, (C3-C6)cycloalkyl, (C2-C6)alkynyl and (C1-C6)haloalkyl; or alternatively, R$_1$ and R$_2$ may be taken together with the carbon atoms to which they are attached to form a 3-6 membered ring;

R$_3$, R$_4$ and R$_5$ are independently selected from the group consisting of hydrogen, halogen, —CN, (C1-C3)haloalkyloxy, (C1-C4)alkoxy, (C1-C6)alkyl, (C3-C6)cycloalkyl, (C2-C6)alkynyl and (C1-C6)haloalkyl;

R$_6$ and R$_7$ are each independently selected from the group consisting of hydrogen or methyl;

R$_8$ and R$_9$ are each independently selected from the group consisting of hydrogen, halogen and (C1-C3)alkyl;

R$_{10}$ and R$_{11}$ are each independently selected from the group consisting of hydrogen, halogen and (C1-C3) alkyl;

R$_{12}$ and R$_{13}$ are each independently selected from the group consisting of hydrogen, halogen and (C1-C3) alkyl;

R$_{14}$ and R$_{15}$ are each independently selected from the group consisting of hydrogen, halogen, (C3-C6)cycloalkyl and (C1-C3)alkyl;

R$_{14}$ and R$_{15}$ together with the carbon atom to which they are attached may form a 3-membered carbocyclic ring;

R$_{16}$ and R$_{17}$ are each independently selected from the group consisting of hydrogen, halogen, (C3-C6)cycloalkyl and (C1-C3)alkyl;

R$_{16}$ and R$_{17}$ together with the carbon atom to which they are attached may form a 3-membered carbocyclic ring;

R$_{15}$ and R$_{16}$ together with the carbons atoms to which they are attached may form a nonaromatic ring having 3 to 6 carbon atoms;

V is independently selected from the group consisting of:

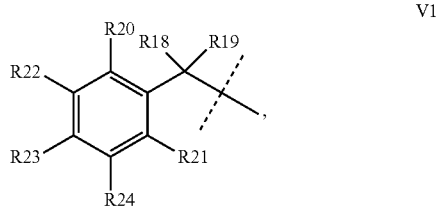

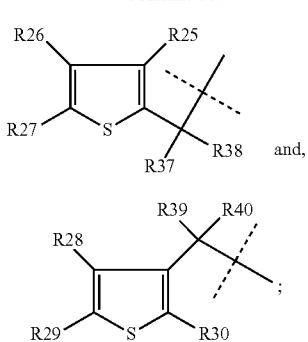

V2

V3

R$_{18}$ and R$_{19}$ are each independently selected from the group consisting of hydrogen or methyl;

R$_{20}$ and R$_{21}$ are each independently selected from the group consisting of hydrogen, (C1-C6)alkyl, or halogen;

R$_{22}$, R$_{23}$ and R$_{24}$ are required to have at least one occurrence independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —NH$_2$, —SH, —OH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, Z$_1$, Z$_2$, Z$_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$;

any remaining open position for substitution for R$_{22}$, R$_{23}$ and R$_{24}$ is independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, Z$_4$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$;

R$_{23}$ and R$_{24}$ may be taken together with the carbon atoms to which they are attached to form a ring;

R$_{34}$ and R$_{35}$ may be together with the nitrogen to which they are attached to form a ring;

R$_{25}$, R$_{26}$ and R$_{27}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, Z$_4$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$;

R$_{28}$, R$_{29}$, and R$_{30}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —NH$_2$, —OH, —SH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, Z$_4$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$;

R$_{26}$ and R$_{27}$ together with the carbons atoms to which they are attached may form a ring;

R$_{28}$ and R$_{29}$ together with the carbons atoms to which they are attached may form a ring;

R$_{31}$ is independently selected from the group consisting of hydrogen, optionally substituted (C1-C8)alkyl, optionally substituted (C3-C9)cycloalkyl, and optionally substituted (C4-C8)alkenyl;

R$_{32}$ is independently selected from the group consisting of optionally substituted (C1-C8)alkyl, optionally substituted (C3-C9)cycloalkyl, and optionally substituted (C4-C8)alkenyl;

R$_{33}$ is independently selected from the group consisting of optionally substituted (C1-C8)alkyl, optionally substituted (C3-C9)cycloalkyl, and optionally substituted (C4-C8)alkenyl;

R$_{34}$ is independently selected from the group consisting of hydrogen, optionally substituted (C1-C8)alkyl, optionally substituted (C3-C9)cycloalkyl, and optionally substituted (C4-C8)alkenyl;

R$_{35}$ is independently selected from the group consisting of hydrogen, optionally substituted (C1-C8)alkyl, optionally substituted (C3-C9)cycloalkyl, and optionally substituted (C4-C8)alkenyl;

R$_{36}$ is independently selected from the group consisting of hydrogen, optionally substituted (C1-C8)alkyl, optionally substituted (C3-C9)cycloalkyl, and optionally substituted (C4-C8)alkenyl;

R$_{37}$ and R$_{38}$ are each independently selected from the group consisting of hydrogen or methyl;

R$_{39}$ and R$_{40}$ are each independently selected from the group consisting of hydrogen or methyl;

with a proviso that R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen;

with a proviso that R$_2$ is —CH$_3$, —Cl, —Br or —OMe then R$_1$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen;

with a proviso that, if R$_3$ is —CH$_3$ or —Cl, then R$_1$, R$_2$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen;

with a proviso that if R$_2$ and R$_3$ are —F, then R$_1$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$ and R$_{24}$ cannot simultaneously be hydrogen;

with a proviso that if $R_{20}$ is —Br and $R_3$ is —CH$_3$, then $R_1$, $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{21}$, $R_{22}$, $R_{23}$ and $R_{24}$ cannot simultaneously be hydrogen;

$Z_1$ is an optionally substituted 6-membered heterocyclic ring containing 1 or 2 heteroatoms;

$Z_2$ is an optionally substituted 4- or 5-membered heterocyclic ring;

$Z_3$ is an optionally substituted 7-, 8- or 9-membered heterocyclic ring;

$Z_4$ is an optionally substituted heterocyclic ring system with 3 to 11 ring atoms;

or a pharmaceutically acceptable salt thereof;

wherein V is V1;

$R_{22}$ is independently selected from (C2-C6)alkynyl and —CN or a pharmaceutically acceptable salt thereof.

2. The compound of claim 1, wherein

V is V1;

$R_{22}$, $R_{23}$ and $R_{24}$ are required to have at least one occurrence independently selected from the group consisting of the following: —NH$_2$, —SH, —OH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_1$, $Z_2$, $Z_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$.

3. The compound of claim 1, wherein

V is V1;

$R_{22}$, $R_{23}$ and $R_{24}$ are required to have at least one occurrence independently selected from the group consisting of the following: —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_2$, $Z_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$.

4. The compound of claim 1, wherein $R_{15}$ is independently selected from halogen and (C1-C3)alkyl;

or a pharmaceutically acceptable salt thereof.

5. The compound of claim 1, wherein $R_{16}$ is independently selected from halogen and (C1-C3)alkyl;

or a pharmaceutically acceptable salt thereof.

6. The compound of claim 1, wherein $R_2$ is independently selected from halogen and (C1-C2)haloalkyl;

or a pharmaceutically acceptable salt thereof.

7. The compound of claim 1, wherein

V is independently selected from V2 and V3;

$R_{26}$ and $R_{28}$ are independently selected from (C2-C6)alkynyl and —CN;

or a pharmaceutically acceptable salt thereof.

8. The compound of claim 1, wherein

V is independently selected from V2 and V3;

$R_{27}$ and $R_{29}$ are independently selected from (C2-C6)alkynyl and —CN;

or a pharmaceutically acceptable salt thereof.

9. The compound of claim 1, wherein

V is V1;

$R_{22}$, $R_{23}$ and $R_{24}$ are required to have at least one occurrence independently selected from the group consisting of the following: halogen, (C1-C6)alkyl, (C3-C9)cycloalkyl, (C3-C9)cycloalkyl(C1-C6)alkyl, (C1-C6)haloalkyl, —NH$_2$, —SH, —OH, (C1-C6)alkoxy, —NR$_{32}$R$_{33}$, substituted (C1-C6)alkyl, substituted (C3-C9)cycloalkyl, substituted (C3-C9)cycloalkyl(C1-C6)alkyl, substituted (C1-C6)haloalkyl, substituted (C1-C6)alkoxy, (C3-C9)cycloalkyl(C2-C6)alkynyl, (C4-C8)cycloalkenyl, (C4-C8)cycloalkenyl(C1-C6)alkyl, $Z_1$, $Z_2$, $Z_3$, aryl, heteroaryl, —CN, —NO$_2$, —SR$_{32}$, —C(O)OH, —C(O)OR$_{32}$, —OC(O)OR$_{32}$, (C2-C6)alkynyl, (C2-C8)alkenyl, (C1-C6)haloalkyoxy, —S(O)$_2$OR$_{32}$, —SO$_2$NR$_{34}$R$_{35}$, —S(O)$_2$R$_{32}$, —NR$_{31}$S(O)$_2$R$_{32}$, —C(O)NR$_{34}$R$_{35}$, —C(O)R$_{31}$, and —NR$_{36}$C(O)R$_{31}$;

or a pharmaceutically acceptable salt thereof.

10. The compound of claim 9, wherein $R_1$ is independently selected from hydrogen and —F;

$R_2$ is independently selected from halogen, (C1-C6)haloalkyl;

$R_3$ is independently selected from hydrogen and —F;

$R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ and $R_{20}$ are simultaneously hydrogen;

$R_{20}$ and $R_{21}$ are independently selected from hydrogen and —F;

or a pharmaceutically acceptable salt thereof.

11. The compound of claim 9, wherein $R_1$ is independently selected from hydrogen and —F;

$R_2$ is independently selected from —CF$_3$, —CHF$_2$, —F, —Cl and —Br;

$R_{22}$ is independently selected from —CN, and —(C2)alkynyl;

$R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{23}$, and $R_{24}$ are simultaneously hydrogen;

or a pharmaceutically acceptable salt thereof.

12. The compound of claim 9, wherein $R_2$ is independently selected from —CF$_3$, —Cl and —Br;

$R_{22}$ is independently selected from halogen;

$R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{23}$, and $R_{24}$ are simultaneously hydrogen;

or a pharmaceutically acceptable salt thereof.

13. The compound of claim 1, wherein the compound is selected from the group consisting of:

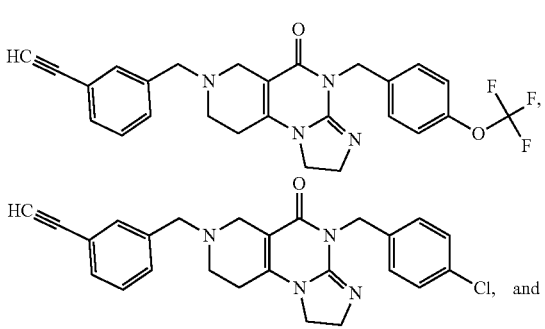

-continued

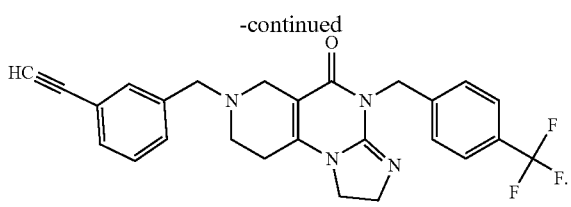

14. The compound of claim 1, wherein the compound is selected from the group consisting of:

and

15. A pharmaceutical composition, comprising a compound of claim 1, or a pharmaceutically acceptable salt thereof, and a pharmaceutically acceptable carrier or excipient.

16. A pharmaceutical composition, comprising a compound of claim 2, or a pharmaceutically acceptable salt thereof, and a pharmaceutically acceptable carrier or excipient.

17. A pharmaceutical composition, comprising a compound of claim 3, or a pharmaceutically acceptable salt thereof, and a pharmaceutically acceptable carrier or excipient.

18. A pharmaceutical composition, comprising a compound of claim 4, or a pharmaceutically acceptable salt thereof, and a pharmaceutically acceptable carrier or excipient.

19. A pharmaceutical composition, comprising a compound of claim 5, or a pharmaceutically acceptable salt thereof, and a pharmaceutically acceptable carrier or excipient.

20. A pharmaceutical composition, comprising a compound of claim 6, or a pharmaceutically acceptable salt thereof, and a pharmaceutically acceptable carrier or excipient.

21. A pharmaceutical composition, comprising a compound of claim 7, or a pharmaceutically acceptable salt thereof, and a pharmaceutically acceptable carrier or excipient.

22. A pharmaceutical composition, comprising a compound of claim 8, or a pharmaceutically acceptable salt thereof, and a pharmaceutically acceptable carrier or excipient.

23. A pharmaceutical composition, comprising a compound of claim 9, or a pharmaceutically acceptable salt thereof, and a pharmaceutically acceptable carrier or excipient.

24. A pharmaceutical composition, comprising a compound of claim 10, or a pharmaceutically acceptable salt thereof, and a pharmaceutically acceptable carrier or excipient.

25. A pharmaceutical composition, comprising a compound of claim 11, or a pharmaceutically acceptable salt thereof, and a pharmaceutically acceptable carrier or excipient.

26. A pharmaceutical composition, comprising a compound of claim 12, or a pharmaceutically acceptable salt thereof, and a pharmaceutically acceptable carrier or excipient.

27. A pharmaceutical composition, comprising a compound of claim 13, or a pharmaceutically acceptable salt thereof, and a pharmaceutically acceptable carrier or excipient.

28. A pharmaceutical composition, comprising a compound of claim 14, or a pharmaceutically acceptable salt thereof, and a pharmaceutically acceptable carrier or excipient.

* * * * *